US010434192B2

(12) United States Patent
Jølck et al.

(10) Patent No.: US 10,434,192 B2
(45) Date of Patent: Oct. 8, 2019

(54) FORMULATION OF SOLID NANO-SIZED PARTICLES IN A GEL-FORMING SYSTEM

(71) Applicant: DANMARKS TEKNISKE UNIVERSITET, Kgs. Lyngby (DK)

(72) Inventors: Rasmus Irming Jølck, Valby (DK); Morten Albrechtsen, Charlottenlund (DK); Lise Nørkjaer Bjerg, Hellerup (DK); Thomas Lars Andresen, Vanlose (DK)

(73) Assignee: DANMARKS TEKNISKE UNIVERSITET, Lyngby (DK)

(*) Notice: Subject to any disclaimer, the term of this patent is extended or adjusted under 35 U.S.C. 154(b) by 0 days.

(21) Appl. No.: 16/050,318

(22) Filed: Jul. 31, 2018

(65) Prior Publication Data
US 2018/0339068 A1 Nov. 29, 2018

Related U.S. Application Data

(62) Division of application No. 14/360,518, filed as application No. PCT/EP2012/073620 on Nov. 26, 2012, now Pat. No. 10,064,960.

(30) Foreign Application Priority Data

Nov. 25, 2011 (EP) ..................................... 11190761
Dec. 16, 2011 (EP) ..................................... 11193947

(51) Int. Cl.
*A61B 5/05* (2006.01)
*A61K 49/04* (2006.01)
(Continued)

(52) U.S. Cl.
CPC ............ *A61K 49/04* (2013.01); *A61B 5/0073* (2013.01); *A61B 6/481* (2013.01); *A61B 6/505* (2013.01);
(Continued)

(58) Field of Classification Search
None
See application file for complete search history.

(56) References Cited

U.S. PATENT DOCUMENTS 3,852,341 A 12/1974 Bjork et al.
4,406,878 A 9/1983 DeBoer
(Continued)

FOREIGN PATENT DOCUMENTS

WO 9403155 A1 2/1994
WO 9519184 A1 7/1995
(Continued)

OTHER PUBLICATIONS

Buyukhatipoglu, K. et al. "Bioprinted Nanoparticles for Tissue Engineering", International Conference on Computational Intelligence for Measurement Systems and Applications, CIMSA 2009, Hong Kong, China May 11-13, 2009; XP031471709.
(Continued)

*Primary Examiner* — Joel F Brutus
(74) *Attorney, Agent, or Firm* — Nath, Goldberg & Meyer; Joshua B. Goldberg; Tanya E. Harkins

(57) ABSTRACT

The present invention relates to novel formulations comprising a plurality of nano-sized solid particles and a gel-forming system, useful, e.g. for imaging of the body of a mammal. Also described are kits comprising such formulations and imaging methods utilizing such formulations or kits.

9 Claims, 14 Drawing Sheets

(51) Int. Cl.
  *B82Y 5/00* (2011.01)
  *A61B 5/00* (2006.01)
  *A61B 6/00* (2006.01)
(52) U.S. Cl.
  CPC ...... *A61K 49/0457* (2013.01); *A61K 49/0485* (2013.01); *B82Y 5/00* (2013.01)

(56) References Cited

U.S. PATENT DOCUMENTS

| | | | |
|---|---|---|---|
| 4,439,356 | A | 3/1984 | Khanna et al. |
| 5,066,580 | A | 11/1991 | Lee |
| 5,198,136 | A | 3/1993 | Tatemoto et al. |
| 5,410,016 | A | 4/1995 | Hubbell et al. |
| 5,750,409 | A | 5/1998 | Herrmann et al. |
| 6,008,379 | A | 12/1999 | Benson et al. |
| 7,871,383 | B2 | 1/2011 | Wiksell et al. |
| 2004/0162505 | A1 | 8/2004 | Kaplan et al. |
| 2005/0080028 | A1 | 4/2005 | Catchpole |
| 2005/0084534 | A1 | 4/2005 | Ni et al. |
| 2005/0147562 | A1 | 7/2005 | Hunter et al. |
| 2005/0234336 | A1 | 10/2005 | Beckman et al. |
| 2007/0092560 | A1 | 4/2007 | Sukuru |
| 2007/0264490 | A1* | 11/2007 | Shimoosako ......... C08G 73/10 428/327 |
| 2007/0275030 | A1 | 11/2007 | Muratoglu et al. |
| 2008/0213189 | A1 | 9/2008 | Lee et al. |
| 2008/0213382 | A1* | 9/2008 | Ivkov ..................... A61K 33/24 424/497 |
| 2008/0241262 | A1 | 10/2008 | Lee et al. |
| 2009/0110738 | A1 | 4/2009 | Gordy et al. |
| 2009/0187199 | A1 | 7/2009 | Gurtner et al. |
| 2009/0264490 | A1 | 10/2009 | Zanella et al. |
| 2010/0290995 | A1* | 11/2010 | Pathak ............... A61K 49/0442 424/9.1 |

FOREIGN PATENT DOCUMENTS

| | | |
|---|---|---|
| WO | 9907416 A1 | 2/1999 |
| WO | 2006075123 A1 | 7/2006 |
| WO | 2006125452 A1 | 11/2006 |
| WO | 2007064152 A1 | 6/2007 |
| WO | 2007064252 A1 | 6/2007 |
| WO | 2007129791 A1 | 11/2007 |
| WO | 2008102127 A2 | 8/2008 |
| WO | 2009150651 A1 | 12/2009 |
| WO | 2011075476 A1 | 6/2011 |
| WO | 2012007567 A1 | 1/2012 |

OTHER PUBLICATIONS

Kim, J-H, et al. "Thermo- and pH-Responsive Hydrogel-Coated Gold Nanoparticles", Chem. Mater. 2004, vol. 16, pp. 3647-3651, XP008102206.
Kim, J.I., et al. "Thermosensitive/magnetic poly(organophosphazene) hydrogel as a long-tern magnetic resonance contrast platform", Biomaterials, vol. 33, pp. 218-224, (2012), XP028333972.
Jing, B. et al. "Sol-Gel-Sol Transition of Gold Nanoparticle-Based Supramolecular Hydrogels Induced by Cyclodextrin Inclusion", ChemPhysChem, vol. 9, pp. 249-252, (2008) XP055053178.
Bakota, et al, "Enzymatic Cross-Linking of a Nanofibrous Peptide Hydrogel", Biomacromolecules 2011, 12, 82-87.
Banta, et al, "Protein Engineering in the Development of Functional Hydrogels", Annu. Rev. Biomed. Eng. 2010.12:167-186.
Bhattarai, et al, "PEG-grafted chitosan as an injectable thermosensitive hydrogel for sustained protein release", Journal of Controlled Release 103 (2005) 609-624.
Bhattarai, et al, "Chitosan-based hydrogels for controlled, localized drug delivery", Advanced Drug Delivery Reviews 62 (2010) 83-99.
Cao, et al, "Comparative study of the use of poly(glycolic acid), calcium alginate and pluronics in the engineering of autologous porcine cartilage", Journal of Biomaterials Science, Polymer Edition, 9:5, 475-487.
Chenite, et al, "Novel injectable neutral solutions of chitosan form biodegradable gels in situ", Biomaterials 21 (2000) 2155-2161.
Cohen, et al, "A novel in situ-forming ophthalmic drug delivery system from alginates undergoing gelation in the eye", Journal of Controlled Release 44 (1997) 201-208.
Collier, et al, "Thermally and Photochemically Triggered Self-Assembly of Peptide Hydrogels", J. Am. Chem. Soc. 2001, 123, 9463-9464.
Couto, et al, "Development of bioactive and biodegradable chitosan-based injectable systems containing bioactive glass nanoparticles", Acta Biomaterialia 5 (2009) 115-123.
Daniel-da-Silva, et al, "Impact of magnetic nanofillers in the swelling and release properties of K-carrageenan hydrogel nanocomposites", Carbohydrate Polymers 87 (2012) 328-335.
De Loos, et al, "Design and Application of Self-Assembled Low Molecular Weight Hydrogels", Eur. J. Org. Chem. 2005, 3615-3631.
Estroff, et al, "Water Gelation by Small Organic Molecules", Chemical Reviews, 2004, vol. 104, No. 3.
Goessl, et al, "A hydrogel system for stimulus-responsive, oxygen-sensitive in situ gelation", Journal of Biomaterials Science, Polymer Edition, 15:7, 895-904.
Gong, et al, "Biodegradable in Situ Gel-Forming Controlled Drug Delivery System Based on Thermosensitive PCL-PEG-PCL Hydrogel: Part 1—Synthesis, Characterization, and Acute Toxicity Evaluation", Journal of Pharmaceutical Sciences, vol. 98, No. 12, Dec. 2009.
Haba, et al, "Preparation of Poly(ethylene glycol)-Modified Poly(amido amine) Dendrimers Encapsulating Gold Nanoparticles and Their Heat-Generating Ability", Langmuir 2007, 23, 5243-5246.
Hartgerink, et al, "Peptide-amphiphile nanofibers: A versatile scaffold for the preparation of self-assembling materials", PNAS, Apr. 16, 2002, vol. 99, No. 8, pp. 5133-5138.
Hindenlang, et al, "Iodine-containing radio-opaque polyphosphazenes", Polym. Chem., 2010, 1, 1467-1474.
Jeong, et al, "In situ gelation of PEG-PLGA-PEG triblock copolymer aqueous solutions and degradation thereof", John Wiley & Sons, Inc. J Biomed Mater Res, 50, 171-177, 2000.
Jeong, et al, "Thermogelling Biodegradable Copolymer Aqueous Solutions for Injectable Protein Delivery and Tissue Engineering", Biomacromolecules 2002, 3, 865-868.
Jeong, et al, "Thermosensitive sol-gel reversible hydrogels", Advanced Drug Delivery Reviews 54 (2002) 37-51.
Kim, et al, "In Vivo Osteogenic Differentiation of Rat Bone Marrow Stromal Cells in Thermosensitive MPEG-PCL Diblock Copolymer Gels", Tissue Engineering, vol. 12, No. 10, 2006.
Klouda, et al, "Thermoresponsive hydrogels in biomedical applications", European Journal of Pharmaceutics and Biopharmaceutics 68 (2008) 34-45.
Umeda, et al, "PEG-Attached PAMAM Dendrimers Encapsulating Gold Nanoparticles: Growing Gold Nanoparticles in the Dendrimers for Improvement of Their Photothermal Properties", Bioconjugate Chem. 2010, 21, 1559-1564.
Kuo, et al, "Ionically crosslinked alginate hydrogels as scalolds for tissue engineering: Part 1. Structure, gelation rate and mechanical properties", Biomaterials 22 (2001) 511-521.
Li, et al, "Cyclodextrin-based supramolecular architectures: Syntheses, structures, and applications for drug and gene delivery", Advanced Drug Delivery Reviews 60 (2008) 1000-1017.
Li et al, "Polyrotaxanes for applications in life science and biotechnology", Appl Microbiol Biotechnol (2011) 90:427-443.
Liu, et al, "A rapid temperature-responsive sol-gel reversible poly(N-isopropylacrylamide)-g-methylcellulose copolymer hydrogel", Biomaterials 25 (2004) 3005-3012.
Wei, et al, "Preparation of Thermosensitive Hydrogels by means of Tandem Physical and Chemical Crosslinking", Macromolecular Research, vol. 19, No. 3, pp. 294-299 (2011).
Loh, et al, "Biodegradable thermosensitive copolymer hydrogels for drug delivery", Expert Opin. Ther. Patents (2007) 17(8):965-977.
Mano, João F., "Stimuli-Responsive Polymeric Systems for Biomedical Applications", Advanced Engineering Materials 2008, 10, No. 6.

(56) References Cited

OTHER PUBLICATIONS

Nagai, et al, "Slow release of molecules in self-assembling peptide nanofiber scaffold", Journal of Controlled Release 115 (2006) 18-25.

Nguyen, et al, "Injectable Biodegradable Hydrogels", Macromol. Biosci. 2010, 10, 563-579.

Peretti et al, "Review of Injectable Cartilage Engineering Using Fibrin Gel in Mice and Swine Models", Tissue Engineering vol. 12, No. 5, 2006.

Petka, et al, "Reversible Hydrogels from Self-Assembling Artificial Proteins", Science vol. 281, Jul. 17, 1998.

Rabin, et al, "An X-ray computed tomography imaging agent based on long-circulating bismuth sulphide nanoparticles", Nature Materials, vol. 5 Feb. 2006.

Rao, et al, "Quick self-healing and thermo-reversible liposome gel", Colloids and Surfaces B: Biointerfaces 82 (2011) 196-202.

Rodriguez, et al, "Cationic cellulose hydrogels: kinetics of the cross-linking process and characterization as pH-/ ion-sensitive drug delivery systems", Journal of Controlled Release 86 (2003) 253-265.

Rozier et al, "Gelrite®: A novel, ion-activated, in-situ gelling polymer for ophthalmic vehicles. Effect on bioavailability of timolol", Journal of Pharmaceutics, 57 (1989) 163-168.

Ruel-Gariepy, et al, "Characterization of thermosensitive chitosan gels for the sustained delivery of drugs", International Journal of Pharmaceutics 203 (2000) 89-98.

Ruel-Gariepy, et al, "A thermosensitive chitosan-based hydrogel for the local delivery of paclitaxel", European Journal of Pharmaceutics and Biopharmaceutics 57 (2004) 53-63.

Ruel-Gariepy, et al, "In situ-forming hydrogels—review of temperature-sensitive systems", European Journal of Pharmaceutics and Biopharmaceutics 58 (2004) 409-426.

Sanborn, et al, "In situ crosslinking of a biomimetic peptide-PEG hydrogel via thermally triggered activation of factor XIII", Biomaterials 23 (2002) 2703-2710.

Schneider, et al, "Self-Assembling Peptide Nanofiber Scaffolds Accelerate Wound Healing", PLoS ONE Jan. 2008 Issue 1 e1410.

Shah, et al, "Cubic phase gels as drug delivery systems", Advanced Drug Delivery Reviews 47 (2001) 229-250.

Song, et al, "Novel casein hydrogels: Formation, structure and controlled drug release", Colloids and Surfaces B: Biointerfaces 79 (2010) 142-148.

Sperinde, et al, "Synthesis and Characterization of Enzymatically-Cross-Linked Poly(ethylene glycol) Hydrogels", Macromolecules 1997, 30, 5255-5264.

Westhaus, et al, "Triggered release of calcium from lipid vesicles: a bioinspired strategy for rapid gelation of polysaccharide and protein hydrogels", Biomaterials 22 (2001) 453-462.

Yeo, et al, "Polymers in the prevention of peritoneal adhesions", European Journal of Pharmaceutics and Biopharmaceutics 68 (2008) 57-66.

Yu, et al, "Injectable hydrogels as unique biomedical materials", Chem. Soc. Rev., 2008, 37, 1473-1481.

Zan, et al, "Covalently Attached, Silver-Doped Poly(vinyl alcohol) Hydrogel Films on Poly(L-lactic acid)", Biomacromolecules 2010, 11, 1082-1088.

Srividya, et al, "Sustained ophthalmic delivery of ofloxacin from a pH triggered in situ gelling system", Journal of Controlled Release 73 (2001) 205-211.

Sun, et al, "Preparation and characterization of a novel injectable in situ cross-linked hydrogel", Polym. Bull. (2009) 62:699-711.

Van de Wetering, et al, "Poly(ethylene glycol) hydrogels formed by conjugate addition with controllable swelling, degradation, and release of pharmaceutically active proteins", Journal of Controlled Release 102 (2005) 619-627.

* cited by examiner

Gelling mechanisms

(A) Temperature change:

(B) Ion strength:

(C) pH:

(D) Enzymatic activity:

■ Peptide ⌇ Scaffold (E) Initiator:

■ Acrylate ⌇ Scaffold (F) Hydration:

Mixture of organic solvent
and/or water

Ion sensitive gel forming systems pH sensitive gel forming systems

A) Synthesis of PEGylated Au nanoparticles

B) Alginate hydrogel formation with encapsulated PEGylated Au nanoparticles

A) Synthesis of PEG$_{750}$-PCL$_{2620}$

B) PEG-PCL hydrogel formation with encapsulated PEGylated Au nanoparticles

FORMULATION OF SOLID NANO-SIZED PARTICLES IN A GEL-FORMING SYSTEM

This is a Divisional Application of U.S. patent application Ser. No. 14/360,518, filed May 23, 2014, an application filed as a national stage under 371 of Application No. PCT/EP2012/073620 filed Nov. 26, 2012 and claiming benefit from European Application No. 1190761.4, filed Nov. 25, 2011, and European Application No. 11193947.6, filed Dec. 16, 2011, the content of each of which is hereby incorporated by reference in its entirety.

FIELD OF THE INVENTION

The present invention relates to novel formulations comprising a plurality of nano-sized solid particles and a gel-forming system.

BACKGROUND OF THE INVENTION

Every year more than 12 million people are diagnosed with cancer worldwide and over 7.5 million people die from cancer each year. These numbers are expected to increase because of population growth and due to the lifestyle in the Western world. Radiotherapy is an important part of modern cancer treatment and more than 50% of cancer patients receive radiotherapy at least once. Modern radiotherapy relies on advanced high precision planning, treatment equipment and imaging techniques (such as, e.g., computed tomography (CT), positron-emission tomography (PET) and magnetic imaging resonance (MRI)) in order to deliver high radiation doses to a precisely defined target in patients.

One of the main difficulties in external beam radiotherapy is that both tumors and the surrounding tissue move significantly and unpredictably during radiotherapy; both within each single treatment, and during the whole course of radiotherapy, lasting usually 5-7 weeks. These movements can be dramatic (e.g. several cm within seconds) and may be caused by various factors such as respiration, bladder- and bowel filling, air passing colon, tumor shrinkage and set-up variation of the patient. One way of minimizing this problem is the implantation of markers in or adjacent to the tumor allowing frequent imaging and treatment adaptation. So far, markers have been inserted using long and thick needles, a complicated procedure with a significant risk of complications, which is limiting the practical usefulness of markers in radiotherapy.

Ideally, a tissue marker should enable tracking of tumor movement; be visible on several image modalities; be visible for an extended period (e.g., at least 4 weeks); be non-toxic; and be easy to insert.

WO 94/03155 A1 describes a hydrogel composition prepared from a backbone bonded to a cross-linking agent. The hydrogels may be loaded with therapeutic drugs and diagnostic labels, including x-ray contrast imaging agents for disease diagnostics and treatment.

WO 95/19184 A1 describes polymeric microparticles containing agents for imaging. The particles are prepared by cross-linking (ionotropically gelling) synthetic polyelectrolytes with multivalent ions such as calcium ions. The particles formed have sizes in the micrometer range.

U.S. 2008/0213189 A1 describes nanoparticles based on metal nanocrystals and having a graphitic shell, for use in imaging.

Couto et al. (Acta Biomater., 2009, 5, 115-123) describe a chitosan based thermo-responsive injectable hydrogel containing bioactive glass nanoparticles for bone tissue engineering applications.

Daniel-da-Silva et al. (Carbohydrate Polymers, 2012, 87, 328-335) describe a model drug-delivery system based on a K-carrageean hydrogel containing magnetic ($FeO_4$) nanoparticles.

In view of the above, it is an object of the invention to provide new formulations comprising solid nano-sized particles and gel-forming, low-viscosity systems that are easy to administer parenterally, and wherein the solid particles that can be visualized by one or multiple imaging modalities, including X-ray imaging.

SUMMARY OF THE INVENTION

In a first aspect, the present invention relates to a formulation for use in imaging of the body of a mammal, comprising i) a plurality of solid in-organic particles having a (number) average diameter of 1-500 nm, and ii) an organic gel-forming system.

In a second aspect, the present invention relates to a formulation for use as a tissue marker, preferably an imageable tissue marker, comprising i) a plurality of solid in-organic particles having a (number) average diameter of 1-500 nm, and ii) an organic gel-forming system.

In a third aspect, the present invention relates to a formulation comprising i) a plurality of solid in-organic particles having a (number) average diameter of 1-500 nm, and ii) an organic gel-forming system.

In a fourth aspect, the present invention relates to a kit comprising a syringe, a hypodermal needle adapted to the open end of said syringe, and a formulation according to the preceding aspect.

In a fifth aspect, the present invention relates to the use of the formulation or kit of the preceding aspects in methods of imaging the body of a mammal, optionally in connection with radiotherapy treatment.

For example, in one embodiment, the present invention relates to a method of recording an X-ray image of the body of a mammal, comprising the steps of
  a) providing a formulation comprising a plurality of solid in-organic particles and an organic gel-forming system, wherein said solid in-organic particles have a (number) average diameter of 1-500 nm and comprise or consist of a compound detectable by X-ray imaging;
  b) administering the formulation to a predetermined location of the mammal, and
  c) recording X-ray-based images, such as CT-images, of at least a part of the body which comprises the predetermined location.

In another embodiment, the present invention relates to a method of joint radiotherapy and X-ray imaging of a target tissue in a mammal, comprising the steps of
  a) providing a formulation comprising a plurality of solid in-organic particles and an organic gel-forming system, wherein said solid in-organic particles have a (number) average diameter of 1-500 nm and comprise or consist of a compound detectable by X-ray imaging;
  b) administering the formulation to a predetermined target tissue of the mammal,
  c) recording X-ray-based images, such as CT-images, of at least a part of the body which comprises the target tissue, thereby providing a definition of the target tissue, and
  d) using the definition of the target tissue obtained in c) to direct external beam radiotherapy to the target tissue.

In one embodiment, the present invention relates to a method for directing local administration of a pharmaceutically active agent to a target tissue in a mammal, comprising the steps of a) providing a formulation comprising a plurality of solid in-organic particles and a system for providing a controlled release of the pharmaceutically active agent in time or anatomically, such as but not limited to an organic gel-forming system, wherein said solid in-organic particles have a (number) average diameter of 1-500 nm and comprise or consist of a detectable compound, optionally detectable by X-ray imaging;

b) administering the formulation to a predetermined target tissue of the mammal, c) recording X-ray-based images, such as Computed Tomography (CT)-images, of at least a part of the body which comprises the target tissue, thereby providing a definition of the target tissue, and d) using the definition of the target tissue obtained in c) to direct local administration of a pharmaceutically active agent to the target tissue.

These and other aspects and embodiments of the invention are set forth in more detail below.

DETAILED DESCRIPTION OF THE INVENTION

Figure 1:
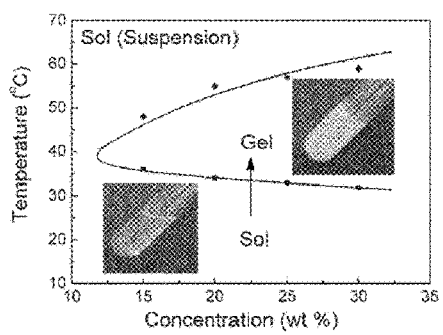
FIG. 1 illustrates various mechanisms of hydrogel formation including thermo-, ion-, pH-, enzymatically-, initiator- and hydration responsive hydrogel forming systems.
Figure 1:
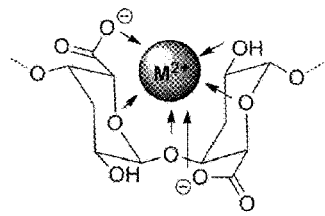
Figure 1:
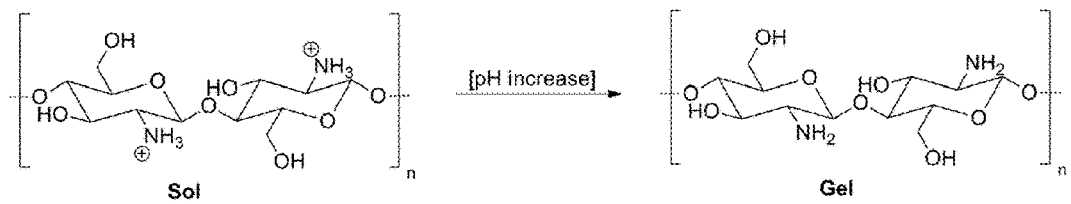
Figure 1:
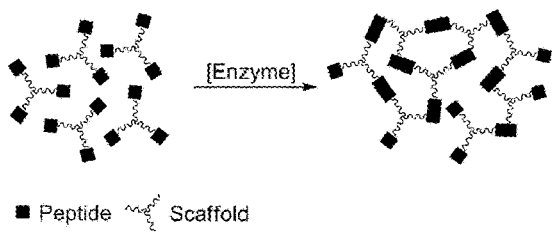
Figure 1:
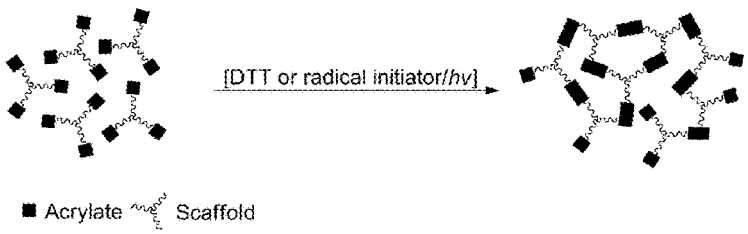
Figure 1:
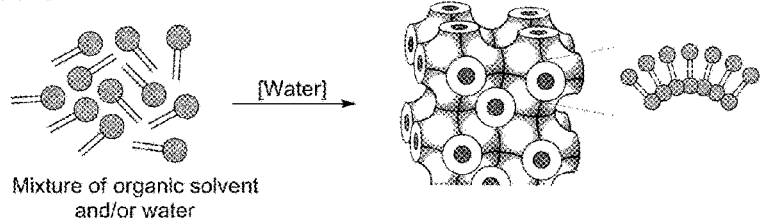

As describe above, the invention relates to a formulation comprising i) a plurality of solid in-organic particles having a (number) average diameter of 1-500 nm, and ii) an organic gel-forming system.

The solid particles typically constitutes 0.001-50% by weight (w/w) of the formulation, e.g. 0.01-30% by weight, such as 0.1-10% by weight, or 0.1-50% by weight of the formulation, e.g. 0.5-30% by weight, such as 0.5-2% or 1-10% by weight.

The formulation is preferably in the form adapted for parenteral administration, and should preferably consist of pharmaceutically acceptable constituents. The formulation which as such has a comparable low viscosity is intended for injection in the body of a mammal, where after the formulation becomes more viscous, i.e. it goes through a sol-gel transition (liquid to gel), due to the presence of the gel-forming system. It is preferred that the viscosity of the formulation after injection in the body of a mammal increases by at least 50%, such as at least 80%, such as at least 100%, or at least 150%, or at least 200%, or at least 300%, or at least 500%, or at least 750%, or at least 1000%, or at least 10,000%, or that the formulation becomes essentially solid (non-viscous).

The formulation is preferably adapted for injection via a thin needle. The viscosity of the hydrogel-forming formulation before injection can be any suitable viscosity such that the formulation can be parenterally administered to a patient. The formulations can be injected with no or minimal back-pressure (for example, less than about 3 Newton (N), or, better, less than about 2 N, or even better, less than about 1 N) via a hypodermal needle having a diameter corresponding to a gauge (G) number of G17 or less, such as G19 or less, such as G21 or less, such as G23 or less, such as G25 or less, such as G25.

Exemplary formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 20° C.

Alternative formulations include, but are not limited to, those having a viscosity (prior to administration/injection) lower than 10,000 centipoise (cP), e.g. lower than 2,000 cP, such as 10 to 2,000 cP, such as 20 to 1,000 cP, such as 150 to 350 cP, such as 400 to 600 cP, such as 600 to 1,200 cP or such as 1,000 to 2,000 cP, or 10 to 600 cP, or 20 to 350 cP, at 5° C.

When referred to herein, the (dynamic) viscosity is measured at the specified temperature in accordance with the method described in ASTM D7483.

Hydrogels may be formed either through covalent bond formation or ionic- or hydrophobic interactions. Physical (non-covalent) cross-links may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including temperature, pH, ionic strength, combinations thereof, and the like. Chemical (covalent) cross linking may be accomplished by any of a number of mechanisms, including free radical polymerization, condensation polymerization, anionic or cationic polymerization, step growth polymerization, electrophile-nucleophile reactions, combinations thereof, and the like. FIGS. 1-5 illustrate exemplary hydrogel-forming systems that can be used in the present invention.

The hydrogel compositions may be loaded with the inorganic particles either prior to or during gel formation, such as when the gel is in a sol-state or in transition to the gel-state, e.g., by diffusion into the hydrogel composition. These particles may either be entrapped in the hydrogel matrix without any chemical bond, or they may be bonded, non-covalently or covalently, to the backbone or cross-linking agent of the hydrogel.

After injection, the gelled formulation typically provides a well defined assembly of solid particles which provides contrast in e.g. X-ray imaging, and which may serve as a marker, thus, enabling tracking of tumor movement during e.g. radiotherapy or surgical procedures.

In the context of the present invention, a "marker" or "tissue marker" is a detectable agent or composition which does not move, or stays substantially in the same position, for several days or weeks once it has been administered or implanted into a specific site or tissue of a mammalian body. A tissue marker can, for example, comprise one or more X-ray contrast agents, radioactive compounds, paramagnetic compounds, fluorescent agents, or other detectable agents.

An "imageable tissue marker" or "imageable marker" comprises a detectable agent in a form and/or a sufficient amount to allow for detection of the tissue marker by an external imaging modality if administered or implanted into a mammalian body. Exemplary external imaging modalities include, but are not limited to, X-ray imaging, CT imaging, MRI, PET imaging, single photon emission computed tomography (SPECT) imaging, nuclear scintigraphy imaging, ultrasonography imaging, ultrasonic imaging, near-infrared imaging and/or fluorescence imaging.

The Solid Inorganic Particles

The solid particles typically have a number average diameter of 1 nm-50 μm, such as 1-500 nm. In some embodiments, the number average diameter is in the range of 5-150 nm, such as 8-50 nm, or 10-20 nm. The number average diameter can be determined using transmission electron microscopy (TEM) or dynamic light scattering (DLS).

Contrast Agents:

The solid particles should preferably be visible by at least CT imaging. Preferred solid particles thus comprise, or consist of, one or more X-ray contrast agents, i.e., compounds that are able to block or attenuate X-ray radiation. Such compounds include transition metals, rare earth metals, alkali metals, alkali earth metals, other metals, as defined by the periodic table. A metal or alkali metal may appear in non-oxidized or any of the existing oxidation states for the metal. These oxidation states include monovalent cations, divalent cations, trivalent cations, tetravalent cations, pentavalent cations, hexavalent cations and heptavalent cations.

In one embodiment, the one or more X-ray contrast agents are selected from gold (Au), bismuth (Bi), gadolinium (Gd), iron (Fe), barium (Ba), calcium (Ca) and magnesium (Mg). In a particular embodiment, the detectable compound comprises one or more compounds selected from the group of gold (Au) and bismuth (Bi). In one particular embodiment, the detectable compound comprises gold (Au). The one or more X-ray contrast agents are typically present in metal form, in alloy form, in oxide form or in salt form.

It should be understood that besides particles which provides a useful contrast for X-ray imaging, the formulation may also include solid particles that are visible in imaging modalities other than X-ray imaging. In one embodiment, the solid-particles are furthermore visible by MR and/or PET imaging, or by other imaging modalities.

In a particular embodiment, the one or more solid particles may further comprise a radioactive or paramagnetic compound for one or more imaging modalities such as MRI, PET imaging, SPECT imaging, nuclear scintigraphy imaging, ultrasonography imaging, ultrasonic imaging, near-infrared imaging and/or fluorescence imaging.

Hence, in some interesting embodiments, the formulation according to any one of the preceding claims, wherein the solid particles further comprise one or more radioactive, paramagnetic or ferromagnetic particles.

Moreover, individual particles may comprise two or more types of compounds which are visible in different imaging modalities.

Said radioactive compounds may comprise isotopes of Copper ($^{61}$Cu, $^{64}$Cu, and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), Zirconium ($^{89}$Zr) and Radium ($^{223}$Ra, $^{224}$Ra), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Said paramagnetic or ferromagnetic compounds may also be selected from the group of Scandium (Sc), Yttrium (Y), Lanthanum (La), Titanium (Ti), Zirconium (Zr), Hafnium (Hf), Vandium (V), Niobium (Nb), Tantalum (Ta); Chromium (Cr), Molybdenium (Mo), Tungsten (W), Manganese (Mn), Technetium (Tc), Rhenium (Re), Iron (Fe), Ruthenium (Ru), Osmium (Os), Cobalt (Co), Rhodium (Rh), Iridium (Ir), Nickel (Ni), Palladium (Pd), Platinum (Pt), Copper (Cu), Silver (Ag), Gold (Au), Zinc (Zn), Cadmium (Cd), Mercury (Hg), the lanthanides such as Lathanum (La), Cerium (Ce), Praseodymium (Pr), Neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu)) and the actinides such as Actinium (Ac), Thorium (Th), Protactinium (Pa), Uranium (U), Neptunium (Np), Plutonium (Pu), Americium (Am), Curium (Cm), Berkelium (Bk), Californium (Cf), Einsteinium (Es), Fermium (Fm), Mendelevium (Md), Nobelium (No) and Lawrencium (Lr), wherein said paramagnetic or ferromagnetic compounds may appear in any of the existing oxidation states for the metal. These oxidation states include monovalent cations, divalent cations, trivalent cations, tetravalent cations, pentavalent cations, hexavalent cations and heptavalent cations.

Said one or more radioactive, paramagnetic or ferromagnetic compounds may be covalently linked to the nano-sized particle or non-covalently associated with the nano-sized particle.

In one embodiment, the nano-sized particles further comprise one or more fluorophore compounds for near infrared fluorescence imaging. Said compounds may comprise a fluorescent proteins, peptides, or fluorescent dye molecules. Common classes of fluorescent dyes include xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Typical fluorescein dyes include 5-carboxyfluorescein, fluorescein-5-isothiocyanate and 6-carboxyfluorescein; examples of other fluorescein dyes can be found, for example, in U.S. Pat. Nos. 6,008,379, 5,750,409, 5,066,580, and 4,439,356. The species may also include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED), and other rhodamine dyes. The species may alternatively include a cyanine dye, such as, for example, Cy3, Cy3B, Cy3.5, Cy5, Cy5.5, Cy. Or IRDye 800CW, IRDye 680LT, Qdot 800 nanocrystal, Qdot 705 nanocrystal or porphyrazine compounds In another embodiment, the nano-sized particles further comprise or consist of one or more gasses encapsulated in lipid, polymer or inorganic based particles for ultrasonography imaging. Said gasses may comprise air, sulphur halides such as sulphur hexafluoride or disulphur decafluoride; fluorocarbons such as perfluorocarbons; fluorinated (e.g. perfluorinated) ketones such as perfluoroacetone; and fluorinated (e.g. perfluorinated) ethers such as perfluorodiethyl ether. Representative perfluorocarbons, which may for example contain up to 7 carbon atoms, include perfluoroalkanes such as perfluoromethane, perfluoroethane, perfluoropropanes, perfluorobutanes (e.g. perfluoro-n-butane, optionally in a mixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane; and mixtures of any of the foregoing, including mixtures with gases such as nitrogen, carbon dioxide, oxygen etc, but not limited to those.

Coating:

The solid particles may further comprise a variety of other components. Useful solid particles include uncoated or coated metal particles, uncoated or coated solid metal salts, as well as liposomes, polymersomes, dendrimers, water-soluble cross-linked polymers, and micelles comprising such solid particles.

As used herein, a solid particle which is "coated" comprises a shell or surface coating around a solid core material. The shell or surface coating can be attached to the core material covalently, non-covalently, or by a mixture of covalent and non-covalent bonds. Exemplary shell or surface coatings are described herein.

In one embodiment, the solid particle comprises a polymer surface coating non-covalently attached to the particle core surface. In one embodiment, the polymer coating comprises polyethylene glycol (PEG), typically with a PEG molecular weight from 2,000 to 70,000 Daltons, such as 5,000 Daltons; dextrans, typically with a molecular weight between 2,000 and 1,000,000 Daltons; and/or hyaluronic acid, typically with a molecular weight between 2,000 and 1,000,000 Daltons. The polymers are typically combined as block copolymers in such a way that the overall polymer structure in negatively charged, allowing electrostatic interaction with a positively charged nano-sized particle surface to achieve efficient coating.

In a particular embodiment, the solid particles comprise conjugated $PEG_{1000}$, $PEG_{2000}$, $PEG_{3000}$, $PEG_{5000}$ or $PEG_{10000}$, i.e., PEG preparations having an average molecular weight of approximately 1,000, 2,000, 3,000, 5,000 and 10,000 Daltons, respectively, but not limited to those.

In one embodiment, the solid particle comprises a polymer surface coating comprising poly(N-isopropylacrylamide) (PNIPAM), typically with a PNIPAM molecular weight from about 500 to about 70,000 Daltons, such as about 1,000 to about 10,000 Daltons, such as about 2,000 to about 5,000 Daltons, such as about 3,500 Daltons. The PNIPAM coating may induce thermoresponsive properties to the particles allowing a change in the hydrophobic properties of the particles as a function of temperature.

In one embodiment, the solid particles comprise a shell or surface coat comprising a lipid layer such as a lipid monolayer and/or one or more lipid bilayers, and a particle core comprising an inorganic particle. The hydrophobic moiety of the surface binding molecules is selected from among alkyl moieties, alkene moieties, alkyne moieties, aryl moieties, hydrophobic moieties of fatty acids or lipids, steroid moieties, and combinations thereof. In other embodiments, the hydrophobic moiety of the surface binding molecules of is selected from among alkyl moieties, alkene moieties, hydrophobic moieties of fatty acids or lipids, and combinations. Hydrophobic surface anchors are selected from among alkyl thiols, alkyl amines, alcohols, and carboxylic acids. In some embodiments, the surface binding molecules are selected from among alkyl thiols and fatty acids. In some embodiments the surface binding molecules are selected from among ($C_{8-20}$)alkyl thiols and ($C_{8-20}$)alkyl fatty acids.

Surface-coating lipids for the purpose of the present invention include, for example, detergents, soaps, emulsifiers, surfactants, saturated fatty acids, unsaturated fatty acids, bile salts, monoglycerides, diglycerides, phospholipids, glycerophospholipids, sphingolipids, sterol lipids, sugar-linked lipids (glycolipids), protein linked lipids, aliphatic alcohols, steroids, and derivatives thereof. Specific, non-limiting examples of such surface-coating lipids include sorbitan monolaurate, polyoxyethylene (20) sorbitan monolaurate (Tween® 20), sorbitan monopalmitate, polyoxyethylene (20) sorbitan monopalmitate (Tween® 40), sorbitan monostearate, polyoxyethylene (20) sorbitan monostearate (Tween® 60), sorbitan monooleate, and polyoxyethylene (20) sorbitan monooleate (Tween® 80). In some other embodiments, the amphiphilic molecules are selected from among phosphatidic acid, phosphatidylcholine, phosphatidylserine, phosphatidylglycerol, phosphatidylethanolamine, phosphatidylinositol, and bisphosphatidyl glycerol. In yet some other embodiments, the amphiphilic molecules are selected from among sodium dodecylsulfate, sodium cholate, sodium deoxycholate, taurocholic acid, N-lauroyl-sarcosine sodium salt, lauryldimethylanlineoxide, cetyltrimethyl ammonium bromide, and bis(2-ethylhexyl)sulfosuccinate sodium salt. In other embodiments, the amphiphilic molecules are selected from among butyric acid, lauric acid (dodecanoic acid), myristic acid (tetradecanoic acid), palmitic acid (hexadecanoic acid), stearic acid (octadecanoic acid), arachidic acid (eicosanoic acid), linolenic acid, alpha-linolenic acid, docosahexaenoic acid, eicosapentaenoic acid, linolenic acid, arachidonic acid, oleic acid, erucic acid, stearidonic acid, eicosatetraenoic acid, gannlla-linolenic acid, dihomo-gamma-linolenic acid, arachidonic acid, and alkali metal salts thereof.

Specific, non-limiting examples of solid particles are gold nano-sized particles synthesized with a PEG coating or PEGylated gold nanorods as described in WO 2007/129791 and Kim et al 2007 [Invest. Radiol., 2007, 42, 797-806], polymer-coated bismuth sulphide nano-sized particles as described in Rabin 2006 [Nat. Mater., 2006, 5, 188-122], calcium phosphate liposome core-shell nanocomposites, dendrimers of PAMAM with entrapped gold nano-sized particles for CT imaging as described in Haba et al. 2007 [Langmuir, 2007, 23, 5243-5246] and Kojima et al 2010 [Bioconjugate Chem., 2010, 21, 1559-1564] and other solid particles comprising X-ray contrast agents known in the art. In a specific embodiment of the present invention, the shell of the nano-sized particle comprises 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C", and 1,2-distearoyl-sn-glycero-3-phosphoethanolamine-N-[methoxy (polyethylene glycol)-2000]-TATE (DSPE-PEG-2000-RGD) "D" with the molar ratio A:B:C:D, wherein A is selected from the interval 45 to 65, B is selected from the interval 35 to 45, C is selected from the interval 5 to 13, D is selected from the interval 0 to 3, and wherein A+B+C+D=100.

The solid particles may additionally comprise a shell or surface coat which can be covalently detached from the particle upon internal or external stimuli. Internal stimuli such biological activation (e.g. enzymatic cleavage, hydrolysis, reduction, oxidation etc.) or external stimuli such as e.g. electromagnetic radiation e.g. UV-radiation may alter the particle composition and change their in vivo performance.

Enzymatic sensitive coatings may be designed by incorporating a peptide sequence between the surface of the particle and the coating, which is configured for cleavage by an enzyme, such as a protease (e.g. pepsin, trypsin, thermolysine or matrix metalloprotease (MMP)) (FIG. 5d), a glycosidase (e.g. α-, β-, γ-amylase, α-, β-glucosidase or lactase) or an esterase (e.g. acetyl cholinesterase, pseudo cholinesterase or acetyl esterase). Other enzymes which may cleave the cleavable linker include urokinase plasminogen activator (uPA), lysosomal enzymes, cathepsins, prostate-specific antigen, Herpes simplex virus protease, cytomegalovirus protease, thrombin, caspase, and interleukin 1 beta converting enzyme. Still another example is over-expression of an enzyme, e.g. of proteases (e.g. pepsin, trypsin), in the tissue of interest, whereby a specifically designed peptide linker will be cleaved in upon arrival at the tissue of interest. Illustrative examples of suitable linkers in this respect are; Gly-Phe-Ser-Gly, Gly-Lys-Val-Ser, Gly-Trp-Ile-Gly, Gly-Lys-Lys-Trp, Gly-Ala-Tyr-Met.

Another example pH sensitive linkers which are cleaved upon a change in pH, e.g. at low pH, which will facilitate hydrolysis of acid (or base) labile moieties, e.g. acid labile ester groups etc. Such conditions may be found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. Other examples of pH-sensitive linkages include acetals, ketals, activated amides such as amides of 2,3 dimethylmaleamic acid, vinyl ether, other activated ethers and esters such as enol or silyl ethers or esters, imines, iminiums, enamines, carbamates, hydrazones, and other linkages.

External stimuli such as e.g. electromagnetic radiation e.g. UV-radiation may additionally be used to covalently detach the coating from the particle. The amount of contrast agent comprised within the nano-sized particles according to the present invention may be quantified by the weight percent of the contrast agent relative to the total weight of the nano-sized particle, excluding any water comprised by the nano-sized particle, by defining the weight percent of the contrast agent relative to the weight of the shell of the nano-sized particle, or by quantifying the size of the contrasting agent within the prepared nano-sized particles. The latter can be measured by conventional methods in the art, such as cryo-transmission electron microscopy or dynamic light scattering.

In one embodiment, the detectable compound has a weight percent of at least 10% compared to the total weight of the nano-sized particle excluding water, such as at least 50%, such as at least 95%, such as between 95% to 99%, or about 100% of the weight percent relative to the total weight of the nano-sized particle excluding any water.

In one embodiment, the particle core comprising or consisting of the contrast agent has a number average diameter in the range of 1 to 148 nm.

Shape and Size:

The nano-sized particles according to the present invention can be quasi spherical, spherical or non-spherical such as rod-shaped. Suitable nanoparticles include those having a size up to 50 µm, preferably up to 5 µm.

Preferably, the nano-sized particles according to the present invention are of a size in the range of 1 to 500 nm, such as 2 to 10 nm, or such as 10 to 100 nm, such as 10 to 80 nm, such as 10 to 50 nm, such as 10 to 20 nm, such as 10 to 15 nm, or such as 15 to 20 nm, or such as 20 to 50 nm, or such as 50 to 80 nm, or such as 80 to 110 nm, or such as 110 to 140 nm, or such as 140 to 170 nm, or such as 170 to 200 nm or such as 200 to 220, or such as 220 to 250 nm, or such as 250 to 280 nm, or such as 280 to 310 nm, or such as 310 to 340 nm, or such as 340 to 370 nm, or such as 370 to 400 nm, or such as 400 to 420, or such as 420 to 450 nm, or such as 450 to 480 nm, or such as 480 to 500 nm. The size may according to the present invention be measured in terms of the diameter, length or width, including the number average diameter, length or width.

In a preferred embodiment, the nano-sized particles in the composition of the present invention have a number average diameter in the range of 10 nm to 150 nm, such as 10 to 100 nm, such as 10 to 80 nm, such as 10 to 50 nm, such as 10 nm to 30 nm, such as 10 nm to 20 nm, or such as 30 nm to 40 nm, or such as 40 nm to 50 nm, or such as 50 nm to 60 nm, or such as 60 nm to 70 nm, or such as 70 nm to 80 nm, or such as 90 nm to 100 nm, or such as 100 nm to 110 nm, or such as 110 nm to 120 nm, or such as 120 nm to 130 nm, or such as 130 nm to 140 nm, or such as 140 nm to 150 nm.

Controlling the shape and the size of the nano-sized particles may have significant influence on the stability of the nano-scale colloidal suspensions as well as the in vivo fate of the particles. In a preferred embodiment, the nano-sized particles in the composition of the present invention have a number average diameter in the range of 10 nm to 100 nm. Such nano-sized particles exhibit low/no sedimentation rate due to the effects of Brownian motion.

In another preferred embodiment, the nano-sized particles in the composition of the present invention have a number average diameter <10 nm. Such particles may be cleared, after degradation of the hydrogel, by e.g. renal filtration with subsequently excretion into the urine, which may prevent prolonged tissue retention and/or thus lower the risk of toxicity.

The Organic Gel-Forming System

Suitable gel-forming components include, but are not limited to, those composed of organic constituents such as polymers, lipids, peptides, proteins, low molecular weight gelators and non-water soluble high-viscosity liquid carrier materials as well as combinations hereof.

The polymer may be a homopolymer, a copolymer, block copolymer, or a graft copolymer, or a dendrimer-type copolymer of synthetic or natural origin. Specific examples of suitable monomers may include: Lactide, glycolide, N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinyl sulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. Other monomers may include: acrylate derivatives and methacrylate derivatives such as ethyl acrylate, methyl methacrylate, and glycidyl methacrylate; N-substituted alkyl methacrylamide derivatives such as N-n-butyl methacrylamide; vinyl chloride, acrylonitrile, styrene, vinyl acetate, lactones such as ε-caprolactone, lactames such as ε-caprolactame and the like. Additional examples of suitable monomers include alkylene oxides such as propylene oxide, ethylene oxide and the like, but not restricted to any of these specific examples.

On the other hand, specific examples of polymeric blocks to be combined with (or bonded to) the above-mentioned monomers may include: methyl cellulose, dextran, polyethylene oxide, polypropylene oxide, polyvinyl alcohol, poly N-vinyl pyrrolidone, polyvinyl pyridine, polyacrylamide, polymethacrylamide, poly N-methyl acrylamide, polyhydroxymethyl acrylate, polyacrylic acid, polymethacrylic acid, polyvinyl sulfonic acid, polystyrene sulfonic acid, and salts of these acids; poly N,N-dimethylaminoethyl methacrylate, poly N,N-diethylaminoethyl methacrylate, poly N,N-dimethylaminopropyl acrylamide, and salts of these, poly lactic-co-glycolic acid, polycaprolactone and combinations hereof, but not limited to those.

The lipid may be any phospholipid including one or more of a sterol such as cholesterol, and cholestanol, a fatty acid having a saturated or unsaturated acyl group having 8 to 22 carbon atoms and an antioxidant such as alpha-tocopherol. Examples of the phospholipids include, for example, phosphatidylethanolamines, phosphatidylcholines, phosphatidylserines, phosphatidylinositols, phosphatidylglycerols, cardiolipins, sphingomyelins, ceramide phosphorylethanolamines, ceramide phosphorylglycerols, ceramide phosphorylglycerol phosphates, 1,2-dimyristoyl-1,2-deoxyphosphatidylcholines, plasmalogens, phosphatidic acids, and the like, and these may be used alone or two or more kind of them can be used in combination. The fatty acid residues of these phospholipids are not particularly limited, and examples thereof include a saturated or unsaturated fatty acid residue having 12 to 20 carbon atoms. Specific examples include an acyl group derived from a fatty acid such as lauric acid, myristic acid, palmitic acid, stearic acid, oleic acid and linoleic acid. Further, phospholipids derived from natural products such as egg yolk lecithin and soybean lecithin can also be used. Also suitable are, for example, di- and tri-glycerides, 1,2-bis(oleoyloxy)-3-(trimethylammonio)propane (DOTAP), 1-N,N-dimethylaminodioleoylpropane (DODAP), 1-oleoyl-2-hydroxy-3-N,N-dimethylamino-propane, 1,2-diacyl-3-N,N-dimethylaminopropane, 1,2-didecanoyl-1-N,N-dimethylamino-propane, 3-beta-[n-[(N',N'-dimethylamino)ethane]-carbamoyl]cholesterol (DC-Chol), 1,2-dimyristyloxypropyl-3-dimethylhydroxyethyl-ammonium bromide (DMRIE), 1,2-dioleoyloxypropyl-3-dimethylhydroxyethylammonium bromide (DORI), and the like, but not limited to those.

A "peptide" or "polypeptide" refers to a string of at least two α-amino acid residues linked together by chemical bonds (for example, amide bonds). Depending on the context, the term "peptide" may refer to an individual peptide or to a collection of peptides having the same or different sequences, any of which may contain only naturally occurring α-amino acid residues, non-naturally occurring α-amino acid residues, or both. The peptide may exhibit self-assembling properties, for example, peptide amphiphiles, and peptides with β-sheet or α-helical forming sequences. The peptides may include D-amino acids, L-amino acids, or combinations thereof. Suitable, naturally-occurring hydrophobic amino acid residues which may be in the self-assembling peptides include Ala, Val, Ile, Met, Phe, Tyr, Trp, Ser, Thr and Gly. The hydrophilic amino acid residues may be basic amino acids (for example, Lys, Arg, His, Orn); acidic amino acids (for example, Glu, Asp); or amino acids that form hydrogen bonds (for example, Asn, Gln). Degradation of L-amino acids produces amino acids that may be reused by the host tissue. L-configured amino acid residues occur naturally within the body, distinguishing peptides formed from this class of compounds from numerous other biocompatible substances. L-configured amino acids contain biologically active sequences such as RGD adhesion sequences. The amino acid residues in the self-assembling peptides may be naturally occurring or non-naturally occurring amino acid residues. Naturally occurring amino acids may include amino acid residues encoded by the standard genetic code, amino acids that may be formed by modifications of standard amino acids (for example pyrrolysine or selenocysteine), as well as non-standard amino acids (for example, amino acids having the D-configuration instead of the L-configuration). Although, non-naturally occurring amino acids have not been found in nature, they may be incorporated into a peptide chain. These include, for example, D-alloisoleucine(2R,3S)-2-amino-3-methylpentanoic:acid, L-cyclopentyl glycine (S)-2-amino-2-cyclopentyl acetic acid. Self-assembling peptides used in accordance with the disclosure may vary in length so long as they retain the ability to e.g. self-assemble to an extent useful for one or more of the purposes described herein. Peptides having as few as two α-amino acid residues or as many as approximately 50 residues may be suitable. In embodiments, α-amino acid analogs can be used. In particular, α-amino acid residues of the D-form may be used. Useful peptides may also be branched. One or more of the amino acid residues in a self-assembling peptide may be functionalized by the addition of a chemical entity such as an acyl group, a carbohydrate group, a phosphate group, a farnesyl group, an isofarnesyl group, a fatty acid group, or a linker for conjugation. This functional group may provide for inter-peptide linkages, or linkages between the peptide and the hydrogel or hydrogel precursor. For example, the hydrophobic portion of an amphiphilic peptide may be functionalized with acetylene groups. Alternatively, either or both ends of a given peptide may be modified. For example, the carboxyl and/or amino groups of the carboxyl- and amino-terminal residues, respectively, may be protected or not protected. Examples of self assembling peptides include the ones disclosed by Nagai, et al. [J. Controlled Release, 2006, 115, 18-25], Schneider et al. [PLoS ONE, 2008, 1, 1-8] and Hartgerink et al. [PNAS, 2002, 99, 5133-5138].

The protein is not particularly limited and may have a molecular weight from 5-500 kDa, such as 20-200 kDa. It may be of natural origin or human engineered protein expressed in accessible biological expression systems such as e.g. yeast, mammalian, and bacterial expression systems. Preferably, is has a responsive domain such as α-helical coiled-coil or leucine zipper domain—but not limited to those, which upon external or internal stimuli results in hydrogel formation which structurally respond to changes in e.g. pH, temperature, and ionic strength. Examples of such proteins include the ones disclosed by Banta et al. [Annu. Rev. Biomed. Eng., 2010, 12, 167-86]

The low molecular weight gelators include any molecule with molecular weight from 100-4,000 Daltons, such as 250-1,000 Daltons with an amphiphilic structure capable of forming a hydrogel. Specific, non-limiting examples of low molecular weight gelators as described in WO 2008/102127 A2, Chem. Rev., 2004, 104, 1201-1217 and Eur. 3. Org. Chem., 2005, 3615-3631.

The non-water soluble high-viscosity liquid carrier materials include, but are not limited to, sucrose acetate isobutyrate (SAIB), stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, behenyerucate, glyceryl phosphates, acetylated sucrose distearate (Crodesta A-IO), and the like.

The hydrogel of the present invention having biodegradability and sol-gel phase transition which depends on pH, temperature, ion-concentration, enzymatic activity, electric field and hydration may be a solution wherein the gel-forming component(s) constitute 0.1-60 wt %, preferably from 0.5-40 wt %, such as 1-35 wt %.

The composition of the aqueous solvent (dispersion medium) should not be particularly limited, and examples include, for example, a buffer such as phosphate buffer, citrate buffer, and phosphate-buffered physiological saline, physiological saline, a medium for cell culture and the like. Although the formulation can be stably dispersed in these aqueous solvents (dispersion media), the solvents may be further added with a saccharide (aqueous solution), for example, a monosaccharide such as glucose, galactose, mannose, fructose, inositol, ribose and xylose, disaccharide such as lactose, sucrose, cellobiose, trehalose and maltose, trisaccharide such as raffinose and melezitose, and polysaccharide such as α-, β-, or γ-cyclodextrin, sugar alcohol such as erythritol, xylitol, sorbitol, mannitol, and maltitol, or a polyhydric alcohol (aqueous solution) such as glycerin, diglycerin, polyglycerin, propylene glycol, polypropylene glycol, ethylene glycol, diethylene glycol, triethylene glycol, polyethylene glycol, ethylene glycol mono-alkyl ether, diethylene glycol mono-alkyl ether and 1,3-butylene glycol. Additives may furthermore be selected from the group consisting of bioavailable materials such as amiloride, procainamide, acetyl-beta-methylcholine, spermine, spermidine, lysozyme, fibroin, albumin, collagen, transforming growth factor-beta (TGF-beta), bone morphogenetic proteins (BMPs), fibroblast growth factor (bFGF), dexamethason, vascular endothelial growth factor (VEGF), fibronectin, fibrinogen, thrombin, proteins, dexrazoxane, leucovorin, ricinoleic acid, phospholipid, small intestinal submucosa, vitamin E, polyglycerol ester of fatty acid, Labrafil, Labrafil M1944CS, citric acid, glutamic acid, hydroxypropyl, isopropyl myristate, Eudragit, tego betain, dimyristoylphosphatidyl-choline, scleroglucan, and the like; organic solvents such as cremophor EL, ethanol, dimethyl sulfoxide, and the like; preservatives such as methylparaben and the like; sugars such as starch and derivatives thereof, sugar-containing polyols such as sucrose-mannitol, glucose-mannitol, and the like; amino acids such as alanine, arginine, glycine, and the like; polymercontaining polyols such as trehalose-PEG; sucrose-PEG, sucrose-dextran, and the like; sugar-containing amino acid such as sorbitol-glycine, sucrose-glycine, and the like; surfactants such as poloxamer of various molecular weights, Tween 20 Tween 80, Triton X-100, sodium dodecyl sulfate (SDS), Brij, and the like; sugar-containing ions such as trehalose-$ZnSO_4$, maltose-$ZnSO_4$, and the like; and bioacceptable salts such as silicate, NaCl, KCl, NaBr, NaI, LiCl, n-$Bu_4NBr$, n-$Pr_4NBr$, $Et_4NBr$, $Mg(OH)_2$, $Ca(OH)_2$, $ZnCO_3$, $Ca_3(PO_4)_2$, $ZnCl_2$, $(C_2H_3O_2)_2Zn$, $ZnCO_3$, $CdCl_2$, $HgCl_2$, $CaCl_2$, $(CaNO_3)_2$, $BaCl_2$, $MgCl_2$, $PbCl_2$, $AlCl_2$, $FeCl_2$, $FeCl_3$, $NiCl_2$, AgCl, AuCl, $CuCl_2$, sodium tetradecyl sulfate, dodecyltrimethylammonium bromide, dodecyltrmethylammonium chloride, tetradecyltrimethylammonium bromide, and the like, but not limited to those.

In one embodiment of the present invention, the content of the additive is from $1\times10^{-6}$–30 wt %, preferably $1\times10^{-3}$ to 10 wt %, based on the total weight of the gel forming component(s).

A preferred injectable medical hydrogel can have one or more, preferably all, of the following features:

(1) In order to be injectable, the system should be in a sol state before administration. The sol state should be of sufficiently low viscosity—typically lower than 10,000 cP, preferably lower than 2,000 cP, at 20° C. (or alternatively lower than lower than 10,000 cP, preferably 2,000 cP, at 5° C.)—to allow for small needle head to alleviate the patient discomfort and simplify insertion procedure.

(2) Gelation via either chemical cross-linking or physical association starts to happen or is complete after injection.

(3) The gels should be biodegradable or gradually dissolvable within a controlled time period, and the products should be cleared/secreted through normal pathways.

(4) The polymer itself and the degradable products should be biocompatible. Likewise, if additives are added, such as cross-linking agents, initiators etc. these should also be biocompatible.

(5) The gel could potentially have cell/tissue-adhesive properties.

(6) The gel should not result in adverse effects such as immune response, e.g. inflammation.

It should be understood, that the gel-forming system should preferably be biocompatible, i.e. does not stimulate a severe, long-lived or escalating biological response to the formulation when injected into a mammal, in particular a human. To facilitate metabolism of the hydrogel scaffold, degradable linkages can be included through the use of polylactide, polyglycolide, poly(lactide-co-glycolide), polyphosphazine, polyphosphate, polycarbonate, polyamino acid, polyanhydride, and polyorthoester—based building blocks, among others. Additionally, small molecule cross-linking agents containing similar hydrolyzable moieties as the polymers such as carbonates, esters, urethanes, orthoesters, amides, imides, imidoxy, hydrazides, thiocarbazides, and phosphates may be used as building blocks. Additionally, polyglycolide diacrylate, polyorthoester diacrylate and acrylate-substituted polyphosphazine, acrylate-substituted polyamino acid, or acrylate-substituted polyphosphate polymers can be used as degradable building blocks. Methacrylate or acrylamide moieties can be employed instead of acrylate moieties in the above examples. Similarly, small molecules containing a hydrolyzable segment and two or more acrylates, methacrylates, or acrylamides may be used. Such degradable polymers and small molecule building blocks may be functionalized with acrylate, methacrylate, acrylamide or similar moieties by methods known in the art.

In order to be injectability, the system should be in a sol state before administration. The sol state should be of sufficiently low viscosity to allow for small needle head to alleviate the patient discomfort and simplify insertion procedure. Gelation via either chemical cross linking or physical association starts to happen or is complete after injection.

Preferred properties of the gel-forming system include one or more of the following:

Preferably, the gel-forming system is a hydrogel. Hydrogels are comprised of cross-linked polymer networks that have a high number of hydrophilic groups or domains. These networks have a high affinity for water, but are prevented from dissolving due to the chemical or physical bonds formed between the polymer chains. Water penetrates these networks causing swelling, giving the hydrogel its form. Fully swollen hydrogels have some physical properties common to living tissues, including a soft and rubbery consistency, and low interfacial tension with water or biological fluids. The elastic nature of fully swollen or hydrated hydrogels can minimize irritation to the surrounding tissues after implantation. A low interfacial tension between the hydrogel surface and body fluid minimizes protein adsorption and cell adhesion, which reduces the risk of an adverse immune reaction. Many polymers used in hydrogel preparations (e.g. polyacrylic acid (PAA), PHEMA, PEG, and PVA) have mucoadhesive and bioadhesive characteristics that enhance drug residence time and tissue permeability. This adhesive property is due to inter-chain bridges between the hydrogel polymer's functional groups and the mucus glycoproteins, which can help enhance tissue specific binding.

Preferably, before in vivo administration, the gel-forming system according to the invention is a flowable aqueous solution. The solid inorganic particles can, for example, be added to the gel-forming system simply by mixing before injection. Once injected, the gel-forming system rapidly gels under physiological conditions. An injectable matrix can thus be implanted in the human body with minimal surgical procedure. After gelation in situ, the matrix can provide a reference marker for imaging and image-guided radiotherapy.

A number of activators or conditions can be used to trigger this transition upon injection, either externally applied or in response to the tissue micro-environment. Examples of this include gelation as a response to pH, temperature, ion-concentration, enzymatic activity, electric field and hydration (FIG. 1). In relation to the invention it is relevant to be able to tune the mechanical stability within the tissue to allow for single injections.

Gel-Forming System in Response to Temperature Change

In one embodiment, the gel-forming system undergoes gel-formation in response to a temperature in the range of 10-65° C., preferably in the range 35-40° C.

Figure 2:
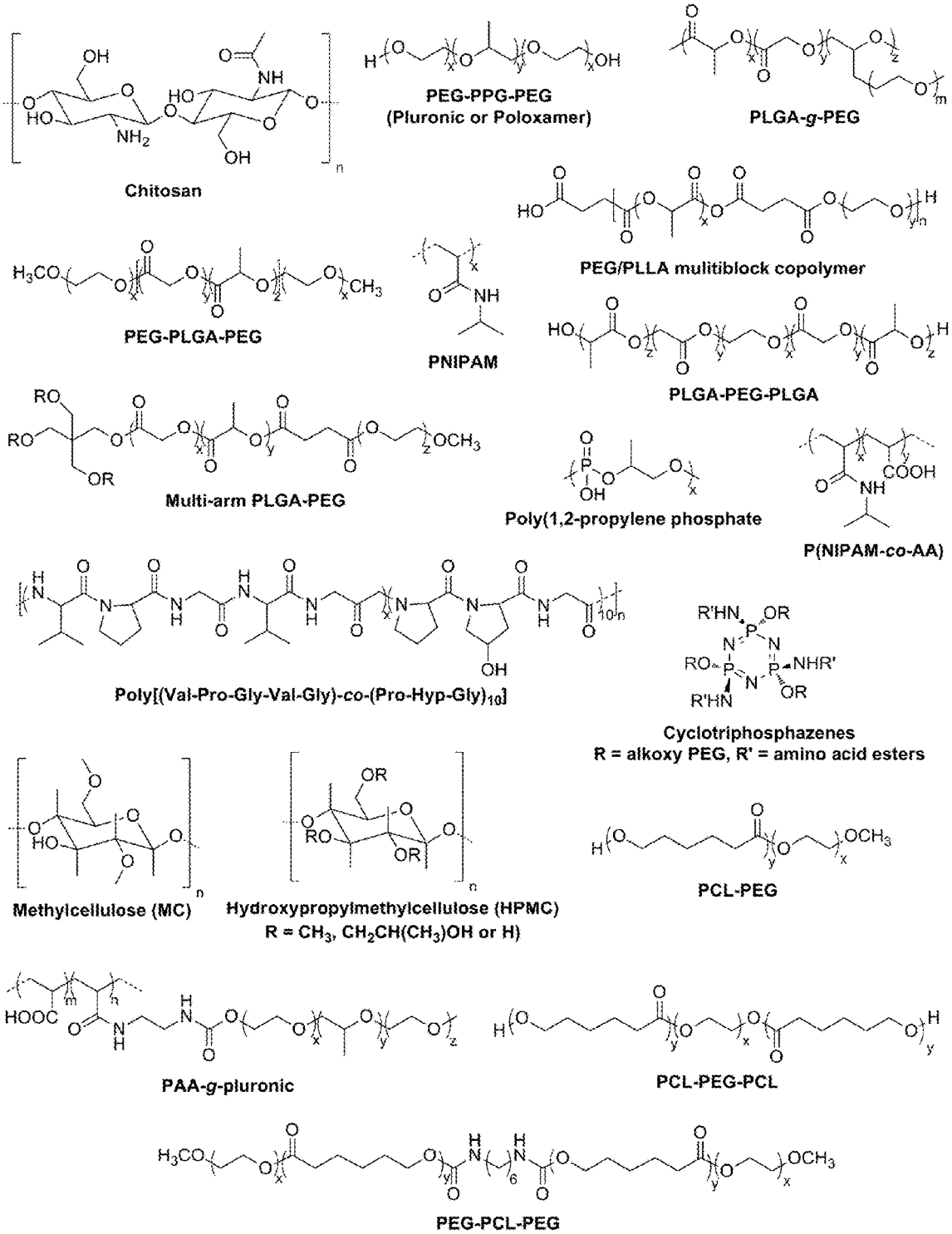
FIG. 2 illustrates various thermo responsive hydrogel forming systems which can exhibit an inverse sol-gel transition.

The favoured thermosensitive material might exhibit an inverse sol-gel transition. The term "inverse" here means that gelation occurs upon heating instead of cooling. Exemplary biodegradable or bioabsorbable thermogelling polymers are shown in FIG. 2. According to the origin of materials, thermogelling hydrogels can be classified into natural (or seminatural) polymeric systems and synthetic polymeric systems. The polymers in the former system include cellulose, chitosan, xyloglucan, gelatin etc. and their derivatives. The polymers in the latter class include some polyethers, block copolymers of polyethers and biodegradable polyesters, synthetic polypeptides, and other polymers (FIG. 2).

Other examples of such gel-forming systems are those described in; i) Eur. J. Pharm. Biopharm., 2004, 57, 53-63, ii) Chem. Soc. Rev., 2008, 37, 1473-1481, iii) Adv. Drug Deliv. Rev., 2010, 62, 83-99, iv) Macromol. Biosci., 2010, 10, 563-579, v) J. Controlled Release, 2005, 103, 609-624, vi) Expert Opin. Ther. Patents, 2007, 17, 965-977, vii) Appl. Microbiol. Biotechnol., 2011, 427-443, viii) Science, 1998, 281, 389-392, ix) Eur. J. Pharm. Biopharm. 2008, 68, 34-45, x) Biomacromolecules, 2002, 4, 865-868, xi) Colloids and Surfaces B: Biointerfaces, 2011, 82, 196-202, xii) Biomacromolecules, 2010, 11, 1082-1088, xiii) Adv. Eng. Mater., 2008, 10, 515-527, xiv) Eur. J. Pharm. Biopharm., 2004, 58, 409-426, xv) Adv. Drug Deliv. Rev., 2002, 54, 37-51, xvi) Biomater., 2004, 25, 3005-3012, xvii) J. Biomed. Mater. Res., 2000, 50, 171-177, xviii) xix) WO 2007/064252 A1, xx) WO 2009/150651, xxi) WO 2007/064152 A1, xxii) WO 99/07416, xxiii) Park K., Shalaby W. S. W., Park H., *Biodegradable hydrogels for drug delivery*. Basel: Technomic Publishing Co., Inc., 1993. ISBN 1-56676-004-6, Print, xxiv) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print—and references herein, but not limited to those.

In one interesting embodiment the thermo sensitive polymer is poly(ethylene glycol)-b-poly(propylene glycol)-b-poly(ethylene glycol) (PEG-PPG-PEG, Pluronic® or Poloxamer) or derivates hereof. By controlling the PEG/PPG composition, the molecular weight and the concentration, reversible gelation can occur at physiological temperature and pH.

In another interesting embodiment the thermo sensitive polymer is chitosan. Chitosan can be a thermally sensitive, pH dependent, gel-forming system by the addition of polyol salts (e.g. β-glycerophosphate, GP). These formulations possess a neutral pH, remain liquid at or below room temperature, and form monolithic gels at body temperature. The stability of the sol at room temperature and the gelation time increase as the chitosan degree of deacetylation decreases [Int. J. Pharm., 2000, 203, 89-98]. The gelation for these chitosan-based systems occurs by the combination of charge neutralization, ionic and hydrogen bonds and, as the main driving force, hydrophobic interaction factors. Additionally, such systems are highly compatible with biological compounds and can be used to inject in vivo biologically active growth factors and cells [Biomater., 2000, 21, 2155-2161].

In one very interesting embodiment the thermo sensitive polymer is poly(caprolactone-b-ethylene glycol-b-caprolactone) (PCL-PEG-PCL), poly(ethylene glycol-b-caprolactone-ethylene glycol) (PEG-PCL-PEG) or poly(ethylene glycol-b-caprolactone) (PEG-PCL). This family of block co-polymers can be tuned to be free flowing solutions at room temperature and strong biodegradable gels at body temperature. Such polymers are highly biocompatible having showed very little toxicity with a maximum tolerance dose of 25 g/kg body weight by subcutaneous administration [J. Pharm. Sci., 2009, 98, 4684-4694] and have been found stabile in vivo for more than 4 weeks [Tissue Eng. 2006, 12, 2863-2873].

In another interesting embodiment the thermo sensitive polymer is poly(ethylene glycol-b-[DL-lactic acid-co-glycolic acid]-b-ethylene glycol) (PEG-PLGA-PEG) triblock copolymers. PEG-PLGA-PEG (33 wt %) is a free-flowing sol at room temperature and become a gel at body temperature. The gel showed good mechanical strength and the integrity of gels persisted longer than 1 month [J. Biomed. Mater. Res., 2000, 50, 171-177]. Additional examples includes poly(N-isopropylacrylamide)-g-methylcellulose copolymer as a reversible and rapid temperature-responsive sol-gel hydrogel. By tuning the methylcellulose content gelation temperature, gelation time and mechanical strength can be controlled [Biomater., 2004, 25, 3005-3012].

Gel-Forming System in Response to Change in Ion-Strength

In another embodiment, wherein the gel-forming system undergoes gel-formation in response to change in ion-strength in the range of 1 μM-500 mM—preferably in the range of 1-50 mM or 50-200 mM.

Figure 3:
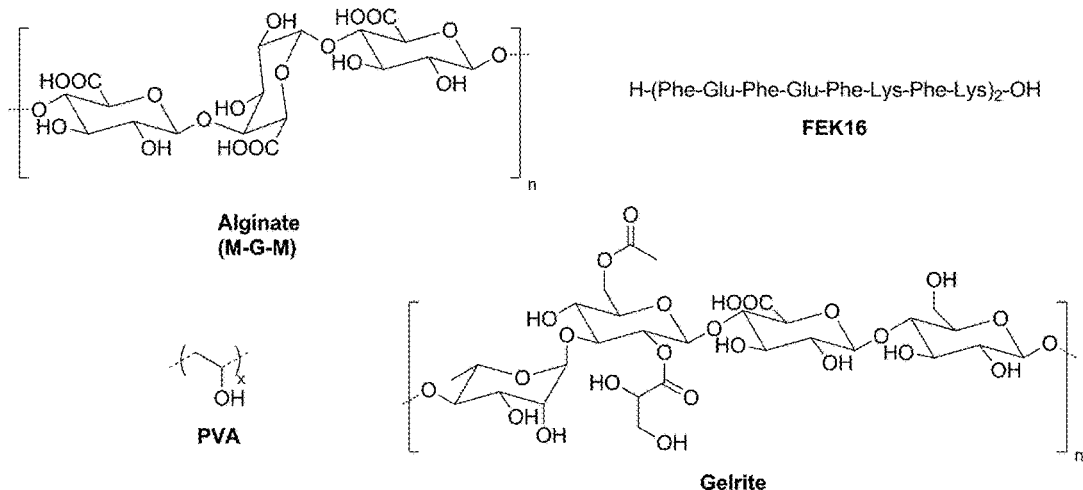
FIG. 3 illustrates various ion sensitive hydrogel forming systems which form gels in high salt concentration.

Non-limiting examples of such gel-forming systems include those illustrated in FIG. 3 and those described in i) Int. J. Pharm. 1989, 57, 163-168, ii) J. Controlled Release, 1997, 44, 201-208, iii) J. Am. Chem. Soc., 2001, 123, 9463-9464, iv) J. Controlled Release, 2003, 86, 253-265, v) Biomater., 2001, 22, 511-521, xi) Park K., Shalaby W. S. W., Park H., *Biodegradable hydrogels for drug delivery*. Basel: Technomic Publishing Co., Inc., 1993. ISBN 1-56676-004-6, Print xii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print; and references cited therein.

One intriguing example of such a gel-forming system is that of alginate. Alginic acid is an unbranched binary copolymer of 1-4 glycosidically linked L-guluronic acid (G) and its C-5 epimer D-mannuronic acid (M). The proportion as well as the distribution of the two monomers determines to a large extent the physiochemical properties of alginate.

In one embodiment, the gel-forming system is based on an aqueous solution of an alginate. Alginates are a family of linear polysaccharides, which, in aqueous solutions, can gel after addition of multivalent cations. The use of alginate as an immobilizing agent in most applications rests in its ability to form heat-stable strong gels which can develop and set at room temperatures. It is the alginate gel formation with calcium ions which has been of interest in most applications. However, alginate forms gels with most di- and multivalent cations. Monovalent cations and $Mg^{2+}$ ions do not induce gelation while ions like $Ba^{2+}$ and $Sr^{2+}$ will produce stronger alginate gels than $Ca^{2+}$. The gel strength depends on the guluronic content and also of the average number of G-units in the G-blocks. Gelling of alginate occur when divalent cations takes part in the interchain binding between G-blocks giving rise to a three-dimensional network in the form of a gel (FIG. 1). The alginate gel as an immobilization matrix is sensitive to chelating compounds such as phosphate, lactate and citrate, presence of anti-gelling cations such as $Na^+$ or $Mg^{2+}$. To avoid this gel beads may be kept in a medium containing a few millimolar free calcium ions and by keeping the $Na^+/Ca^{2+}$ ratio less than 25:1 for high G alginates and 3:1 for low G alginates. An alternative is also to replace $Ca^{2+}$ with other divalent cations with a higher affinity for alginate. There has been found a correlation between mechanical gel strength and affinity for cations. It has been found that gel strength may decrease in the following orders: $Pb^{2+}>Cu^{2+}=Ba^{2+}>Sr^{2+}>Cd^{2+}>Ca^{2+}>Zn^{2+}>Co^{2+}>Ni^{2+}$ However, in applications involving immobilization of living cells toxicity is a limiting factor in the use of most ions, and only $Sr^{2+}$, $Ba^{2+}$ and $Ca^{2+}$ are considered as nontoxic for these purposes. Alginate gels have been found stable in a range of organic solvents.

Since the gel-inducing factor is added before injection, slow physical gelation is required in order to avoid syringe jam. To combat this, calcium ions can be slowly released from, e.g., $CaSO_4$ powder after the powder has been added to a sodium alginate aqueous solution [J. Biomater. Sci. Polym. Ed., 1998, 9, 475-487]. In another interesting embodiment co-injection of the gel-inducing factor and the aqueous alginate solution using a double syringe results in rapid gelation in the tissue of interest thus avoiding syringe jam. Another interesting embodiment is Gellan gum (Gelrite®, FIG. 3)—a high molecular weight polysaccharide (500 kDa) produced by the microbe *Sphingomonas elodea*. Gellan gum is consists of four linked monosaccharides, including one molecule of rhamnose, one molecule of glucuronic acid and two molecules of glucose. It forms gels when positively charged ions (i.e., cations) are added. Thus, the properties of the gel can be controlled by manipulating the concentration of potassium, magnesium, calcium, and/or sodium salts.

In another interesting embodiment the ion-strength sensitive gel-forming system is a peptide such as H-(FEFEFKFK)$_2$-OH (FEK16) which is known to self-assemble into β-sheet structures in an ionic-strength dependent manner [J. Am. Chem. Soc., 2001, 123, 9463-9464]. FEK16 has been found to be highly soluble in pure $H_2O$ but form self-assembled hydrogels at concentrations >10 mg/mL in the presence of mM concentrations of NaCl, KCl, and $CaCl_2$.

Gel-Forming System in Response to Change in pH

In still another embodiment, the gel-forming system undergoes gel-formation in response to changes in pH. Optionally, the gel-forming system undergoes gel-formation in response to a combined change in pH and temperature, such as a pH in the range of 6-8 and a temperature in the range of 35 to 40° C.

Figure 4:
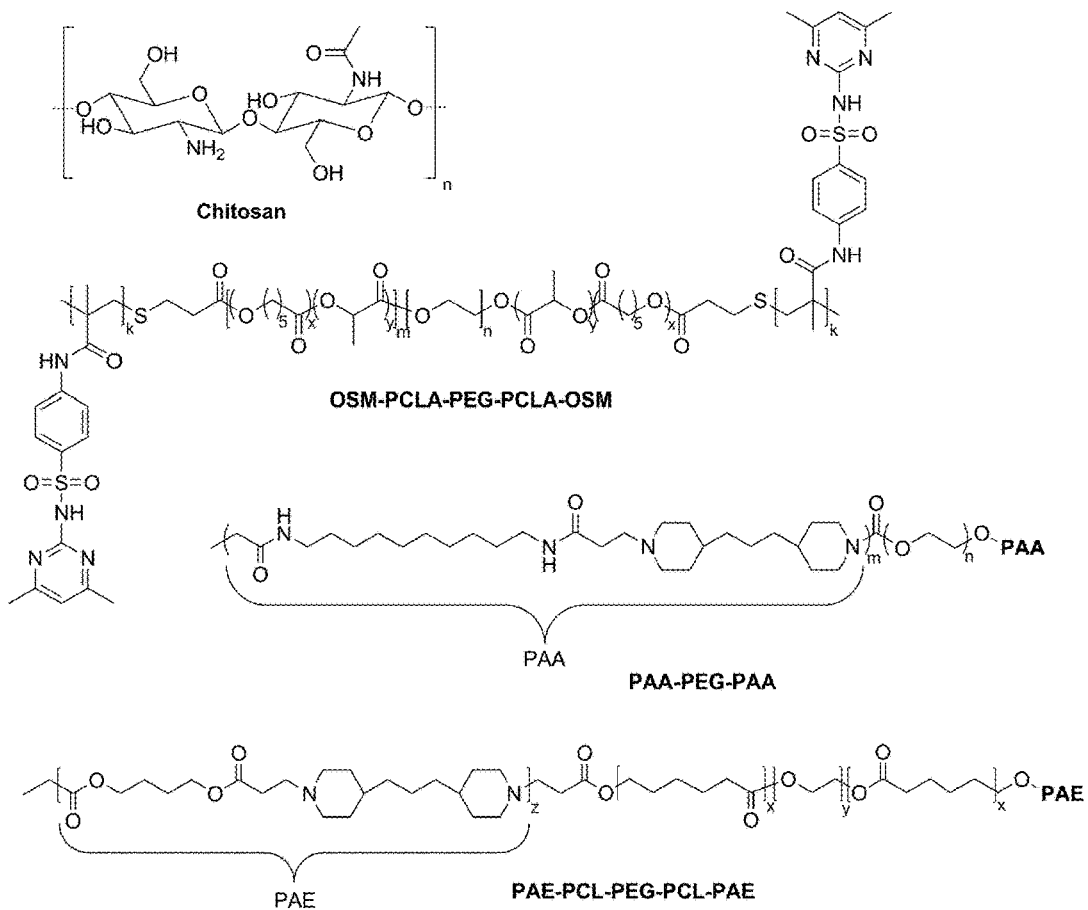
FIG. 4 illustrates various pH sensitive hydrogel forming systems which form hydrogels at specific pH intervals.

Non-limiting examples of such gel-forming systems are illustrated in FIG. 4, and include those described in i) Macromol. Biosci., 2010, 10, 563-579, ii) J. Controlled Release, 2001, 73, 205-211, iii) Topics in tissue engineering—Smart Polymers, Vol. 3, 2007, Chapter 6, iv) Adv. Drug Delivery Rev., 2010, 62, 83-99, v) J. Controlled Release, 2003, 86, 253-265 vi) *Biodegradable hydrogels for drug delivery*. Basel: Technomic Publishing Co., Inc., 1993. ISBN 1-56676-004-6, Print, vii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein.

The pH of the formulation (before injection) is preferably in the range of pH=2-10, optionally in a range selected from 4-6, 6-8 and 8-9.

The properties of pH-responsive hydrogels is highly depending on the $pK_a$ of the ionizable moiety, the hydrophobic moieties in the polymer backbone, their amount and distribution. When ionizable groups become neutral—non-ionized—and electrostatic repulsion forces disappear within the polymer network, hydrophobic interactions dominate. The introduction of a more hydrophobic moiety can offer a more compact conformation in the uncharged state and a more accused phase transition. The hydrophobicity of these polymers can be controlled by the copolymerization of hydrophilic ionisable monomers with more hydrophobic monomers with or without pH-sensitive moieties, such as 2-hydroxyethyl methacrylate, methyl methacrylate and maleic anhydride.

An example of a gel-forming system responsive to pH changes is that which employs the pH-sensitive property of chitosan solutions at low pH. Once injected into the body, these polymer solutions face different environmental pH conditions and form gels. Mucoadhesive pH-sensitive chitosan/glyceryl monooleate (C/GMO) in situ gel system which consisted of 3% (w/v) chitosan and 3% (w/v) GMO in 0.33 M citric acid. Chitosan is normally insoluble in neutral or alkaline pH. However, in dilute acids (pH≤5.0), it becomes soluble due to the protonation of free amino groups on the chitosan chains ($RNH_3^+$). The solubility of chitosan in acidic medium also depends on its molecular weight. Acidic solutions of chitosan when exposed to alkaline pH or body biological pH lose this charge and form viscous gels. Chitosan and GMO both own mucoadhesive property which have been applied in drug delivery system. Positive charges on the chitosan backbone may give rise to a strong electrostatic interaction with mucus or a negatively charged mucosal surface.

Gel-Forming System in Response to Enzymatic Activity

In still another embodiment, the gel-forming system undergoes gel-formation in response to enzymatic activity.

Figure 5:
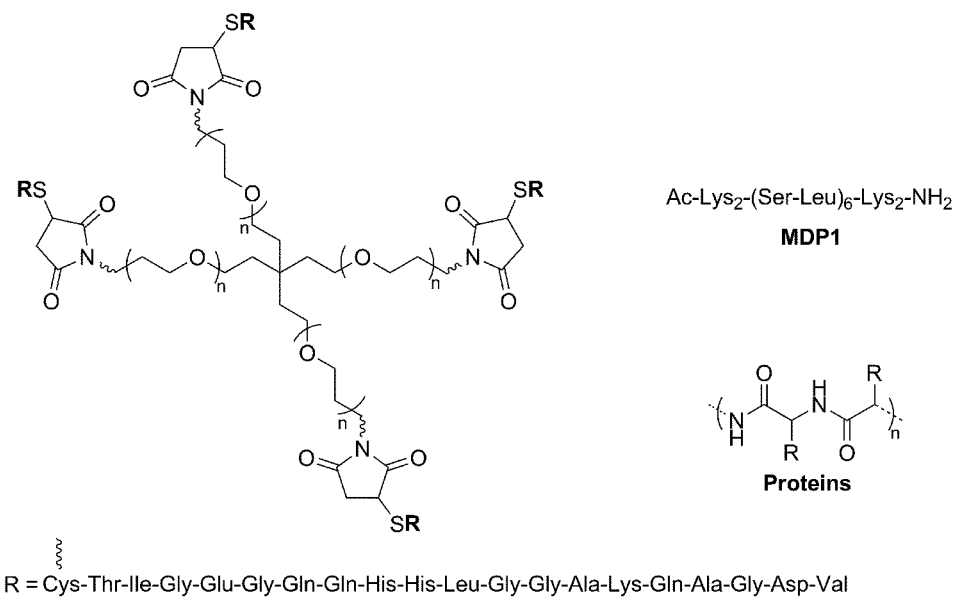
FIG. 5 illustrates various enzymatically sensitive hydrogel forming systems which form hydrogels in presence of specific enzymes.

Non-limiting examples of such gel-forming systems are illustrated in FIG. 5 and include those described in i) Tissue Eng., 2006, 12, 1151-1168, ii) Biomater. 2001, 22, 453-462, iii) Biomater., 2002, 23, 2703-2710, iv) Colloids Surf., B, 2010, 79, 142-148, v) Biomacromolecules, 2011, 12, 82-87, vi) Macromolecules 1997, 30, 5255-5264, vii) *Biodegradable hydrogels for drug delivery*. Basel: Technomic Publishing Co., Inc., 1993. ISBN 1-56676-004-6, Print, viii) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein.

The enzyme or its origin is not particularly limited. It can be added prior, during or after injection of the gel forming system, thus function as a trigger molecule to induce gel formation. It may be encapsulated in a e.g. liposomes etc. which upon exposure to an internal or external stimuli releases the enzyme. Additionally, the enzyme might be present in the injected tissue, either as a natural tissue component, or as a up-regulated enzyme due to the pathophysiological conditions at the site of injection.

In one embodiment, the enzyme triggered gel-forming system is based on caseins, a group of phosphoproteins with a molecular weight in the range from 20 kDa to 30 kDa. Such system can be turned into a hydrogel by addition of microbial transglutaminase (MTGase), a natural tissue enzyme, at physiological temperature and pH [Colloids Surf., B, 2010, 79, 142-148].

Another interesting example of a gel forming system based on enzymatic activation is based on Schiff base formation of lysine rich peptides due to activation by either lysyl oxidase or plasma amine oxidase [Biomacromolecules, 2011, 12, 82-87]. Oxidation of ε-amino groups of lysine by either lysyl oxidase or plasma amine oxidase results in aldehyde formation which readily forms a Schiff base with an additional ε-amino group of lysine resulting in hydrogel formation.

Gel-Forming System in Response to an Initiator

In still another embodiment, the gel-forming system undergoes gel-formation in response to contact with an initiator, e.g. a molecule or irradiation which results in gel formation by cross linking the gel forming system by the means of a covalent chemical bond.

Non-limiting examples of such gel-forming systems are described in i) U.S. Pat. No. 5,410,016, ii) J. Controlled Release, 2005, 102, 619-627, iii) Macromol. Res., 2011, 19, 294-299, iv) Polym. Bull. 2009, 62-699-711, v) J. Biomater. Sci., Polym. Ed., 2004, 15, 895-904, and references cited therein.

In one embodiment the gel forming system is cross linked by photoinitiation by free radical generation, most preferably in the visible or long wavelength ultraviolet radiation. The preferred polymerizable regions are acrylates, diacrylates, oligoacrylates, methacrylates, dimethacrylates, oligomethoacrylates, or other biologically acceptable photopolymerizable groups. Useful photoinitiators for the above mentioned system which can be used to initiate by free radical generation polymerization of the macromers without cytotoxicity and within a short time frame, minutes at most and most preferably seconds. Preferred dyes as initiators of choice for visible light initiation are ethyl eosin, 2,2-dimethoxy-2-phenyl acetophenone, other acetophenone derivatives, and camphorquinone. In all cases, cross linking are initiated among macromers by a light activated free-radical polymerization initiator such as 2,2-dimethoxy-2-phenylacetophenone or a combination of ethyl eosin and triethanol amine, for example.

In another embodiment the gel forming system is cross linked by hetero- or homo bifunctional linkers such as e.g. dithiothreitol, glutaraldehyde, diphenylmethanebismaleimide, dissucinimidyl suberate, bis(sulfosuccinimidyl) suberate, dimethyl adipim and the like, but not limited to those. An example of such a gel forming system is multiacrylate PEG-based polymers which have been reported to form a hydrogel upon addition of the initiator DTT [J. Controlled Release, 2005, 102, 619-627]. The properties the gel could be fine tuned by controlling the size of the polymer and the amount of initiator added and the gel could be formed under physiological temperature and pH. An additional example of such a system is hydrogel formation by chemically cross-linking an hyaluronic acid (HA) derivative with a hydrazide moiety and another HA derivative with an aldehyde, thus, forming a slowly hydrolysable hydrazone bond [Eur. J. Pharm. Biopharm., 2008, 68, 57-66]. This method has the advantage of allowing in situ cross-linking without the use of initiators, cross-linking chemicals, or extra equipment for cross-linking such as a light source.

Gel-Forming System in Response to Hydration

In still another embodiment, the gel-forming system undergoes gel-formation in response to hydration.

Example of such gel-forming systems are those is selected from; i) WO 2006/075123, ii) Adv. Drug Delivery Rev., 2001, 47, 229-250, iii) US 2007/0092560 A1—and references herein, but not limited to those. Formulations composed of neutral diacyllipids and/or tocopherols and/or phospholipids solubilised in biocompatible, oxygen containing, low viscosity organic solvent may form a liquid crystalline phase structure upon hydration, e.g. contact with an aqueous fluid such as extra-vascular fluid, extracellular fluid, interstitial fluid or plasma, but not limited to those. Other systems include non-water soluble high-viscosity liquid carrier materials such as sucrose acetate isobutyrate (SAIB). Such a system may be mixed with solid particles described in the present invention followed by parental injection, thus functioning as a injectable contrast agent which that can be visualized by one or multiple imaging modalities, including X-ray imaging.

Gel-Forming Systems with Cross Linking Groups

In still another embodiment, any of the afore mentioned gel-forming systems, are further functionalized by introducing one or more cross-linkable groups such as acrylate, methacrylate, acrylamide, methacrylamide, vinyl ether, styryl, epoxide, maleic acid derivative, diene, substituted diene, thiol, alcohol, amine, hydroxyamine, carboxylic acid, carboxylic anhydride, carboxylic acid halide, aldehyde, ketone, isocyanate, succinimide, carboxylic acid hydrazide, glycidyl ether, siloxane, alkoxysilane, alkyne, azide, 2'-pyridyldithiol, phenylglyoxal, iodo, maleimide, imidoester, dibromopropionate, and halo acetates, such as bromoacetate, but not limited to those.

Gel-Forming Systems with Chelating Groups

In an additional embodiment, the gel-forming system is comprised of a chelating agent that is known to chelate ions. Any ion chelating agent now known or later discovered may be used in the articles of the present invention. Examples of metal ion (e.g., $Gd^{3+}$ or $Cu^{2+}$) chelating agents include, but are not limited to, expanded porphyrins and porphyrin-like derivatives, DOTA, DTPA, AngioMARK™ (a backbone-functionalized DTPA chelate), DTPA-BMA (a neutral bis-methyl amide derivative of DTPA), and HP-D03A (a DOTA-like macrocyclic compound wherein one chelate arm is replaced with a hydroxylpropyl group). Additional chelates include, but are not limited to, DPDP (TeslaScan™) and Deferoxamine (e.g. $Fe^{3+}$ and $Zr^{4+}$).

Other Constituents of the Formulation

The formulation may further include other constituents, such as α-, β-, and/or γ-cyclodextrins and any derivate hereof. Such constituents may form guest/host complexes with the gel forming system and the nano-sized particles, thus, both aiding in the gel formation and possible alter the particle leakage profile [Adv. Drug Delivery Rev., 2008, 60, 1000-1017]. In one very interesting embodiment the gel forming system is based on PEG-PHB-PEG triblock copolymers, α-cyclodextrin and PEG coated solid nano sized particles. In such a formulation, α-cyclodextrin may form inclusion complexes with both the PEG blocks of the PEG-PHB-PEG triblock copolymers and the PEG coated solid nano sized particles which, combined with hydrophobic interactions between the PHB middle block, forms a strong hydrogel with enhanced retention of solid nano sized particles due α-cyclodextrin interactions which thus altering the particle leakage profile.

The formulation may further comprise compounds or polymers which are visible in imaging modalities other than X-ray imaging.

In one embodiment, the formulation further comprises an iodine-containing polymer, e.g. selected from i) Polym. Chem., 2010, 1, 1467-1474, ii) U.S. Pat. No. 3,852,341, iii) U.S. Pat. No. 4,406,878, iv) U.S. Pat. No. 5,198,136, v) *Biomedical polymers and polymers therapeutics*, Ed. Chiellini E., Sunamoto J., Migliaresi C., Ottenbrite R. M., Cohn D., New York, Kluwer Academic Publishers, 2002, ISBN 0-30646472-1, Print, and references cited therein. Such polymers can be added to the gel forming components prior to gelation and function as contrast agent in vivo. Such polymers may additionally or alternatively be covalently bound to the one or more of the gel forming components or adhered to the particles of the present invention.

The formulation may further comprise pharmaceutically active agents (in short "drugs"; broadly interpreted as agents which are able to modulate the biological processes of a mammal). Examples of pharmaceutically active agents include small drugs, plasmid DNA (e.g. for gene therapy), mRNA, siRNA, carbohydrates, peptides and proteins. Specific examples of pharmaceutically active agents include; a) chemotherapeutic agents such as doxorubicin, mitomycin, paclitaxel, nitrogen mustards, etoposide, camptothecin, 5-fluorouracil, docetaxel irinotecan cisplatin, oxaliplatin and the like; b) radiation sensitizing agents such as porphyrins for photodynamic therapy (e.g. visudyne) or 10B clusters or 157Gd for neutron capture therapy; c) peptides or proteins that modulate apoptosis, the cell cycle, or other crucial signaling cascades; d) Anti inflammatory drugs, such as methylprednisolone hemisuccinate, β-methasone; e) Anti anxiety muscle relaxants such as diclofenac, pridinol; f) Local anesthetics such as lidocaine, bupivacaine, dibucaine, tetracaine, procaine; g) Analgesics such as opiods, non-steroidal anti-inflammatory drugs (NSAIDs); h) Antimicrobial medications such as pentamidine, azalides; i) Antipsychotics such as chlorpromazine, perphenazine; j) The antiparkinson agents such as budipine, prodipine, benztropine mesylate, trihexyphenidyl, L-DOPA, dopamine; k) Antiprotozoals such as quinacrine, chloroquine, amodiaquine, chloroguanide, primaquine, mefloquine, quinine; l) Antihistamines such as diphenhydramine, promethazine; m) Antidepressants such as serotonin, imipramine, amitriptyline, doxepin, desipramine; n) Anti anaphylaxis agents such as epinephrine; o) Anticholinergic drugs such as atropine, decyclomine, methixene, propantheline, physostigmine; p) Antiarrhythmic agents such as quinidine, propranolol, timolol, pindolol; q) Prostanoids such as prostaglandins, thromboxane, prostacyclin, but not limited to those. These drugs can be formulated as a single drug or as a combination of two or more of the above mentioned drugs.

Additional examples of the antitumor agent include camptothecin derivatives such as irinotecan hydrochloride, nogitecan hydrochloride, exatecan, RFS-2000, lurtotecan, BNP-1350, Bay-383441, PNU-166148, IDEC-132, BN-80915, DB-38, DB-81, DB-90, DB-91, CKD-620, T-0128, ST-1480, ST-1481, DRF-1042 and DE-310, taxane derivatives such as docetaxel hydrate, IND-5109, BMS-184476, BMS-188797, T-3782, TAX-1011, SB-RA-31012, SBT-1514 and DJ-927, ifosfamide, nimustine hydrochloride, carboquone, cyclophosphamide, dacarbazine, thiotepa, busulfan, melphalan, ranimustine, estramustine phosphate sodium, 6-mercaptopurine riboside, enocitabine, gemcitabine hydrochloride, carmofur, cytarabine, cytarabine ocphosphate, tegafur, doxifluridine, hydroxycarbamide, fluorouracil, methotrexate, mercaptopurine, fludarabine phosphate, actinomycin D, aclarubicin hydrochloride, idarubicin hydrochloride, epirubicin hydrochloride, daunorubicin hydrochloride, pirarubicin hydrochloride, bleomycin hydrochloride, zinostatin stimalamer, neocarzinostatin, mytomycin C, bleomycin sulfate, peplomycin sulfate, vinorelbine tartrate, vincristine sulfate, vindesine sulfate, vinblastine sulfate, amrubicin hydrochloride, gefitinib, exemestan, capecitabine, TNP-470, TAK-165, KW-2401, KW-2170, KW-2871, KT-5555, KT-8391, TZT-1027, S-3304, CS-682, YM-511, YM-598, TAT-59, TAS-101, TAS-102, TA-106, FK-228, FK-317, E7070, E7389, KRN-700, KRN-5500, 3-107088, HMN-214, SM-11355, ZD-0473 and the like.

Additional examples of radiation sensitizing agents include magnesium 5,10,15,20-tetrakis(4-sulphophenyl)-porphine dodecahydrate, PYROA protein (Emericella nidulans), photosan III, lomefloxacin, cyamemazine, tiaprofenic acid and the like, but not limited to those.

The active compound is included in the composition in an amount sufficient to achieve a desired effect. The amount of drug or biologically active agent incorporated into the composition depends upon the desired release profile, the concentration of drug required for a biological effect, and the desired period of release of the drug. The biologically active substance is typically present in the composition in the range from about 0.5 percent to about 20 percent by weight relative to the total weight of the composition, and more typically, between approximately 1 percent to about 15 percent by weight. Another preferred range is from about 2 percent to about 10 percent by weight. For very active agents, such as growth factors, preferred ranges are less than 1% by weight, and less than 0.0001%.

Viscosity of the Formulation

The viscosity of the formulation is before the injection preferably lower than 10,000 cP, in particular lower than 2,000 cP, at 20° C.

Alternatively, the viscosity of the formulation is before the injection typically lower than 2,000 cP at 5° C.

The organic gel-forming system of the formulation is preferably one which, after injection or under conditions mimicking those in a human body, forms a gel having a viscosity at 37° C. in the range of 2,000 to 50,000,000 cP. More particularly, the viscosity of the hydrogel can be about 2,000 cP, about 5,000 cP, about 10,000 cP, about 20,000 cP, about 30,000 cP, about 50,000 cP, about 75,000 cP, about 100,000 cP, about 125,000 cP, about 150,000 cP, about 200,000 cP, about 30,000 cP, about 800,000 cP, about 1,000,000 cP, about 2,000,000 cP, about 5,000,000 cP, about 10,000,000 cP, about 20,000,000 cP, about 30,000,000 cP, about 40,000,000 cP, about 50,000,000 cP, or ranges thereof. Preferably, the viscosity of the hydrogel after injection (i.e. when present in the desired location) is above 20,000 cP, e.g. in the range of 20,000 cP to 1,000,000 cP. In particular, the formulation after injection is preferably essentially solid.

Specific Embodiments of the Formulation of the Invention

In one embodiment, the gel-forming system comprises alginate. Exemplary formulations comprise a gel-forming system comprising about 0.1 to about 25% w/w alginate, such as about 0.5 to about 10% w/w, about 1 to about 5% w/w, such as about 2% w/w alginate, in aqueous solution. For example, first, an aqueous solution of sodium alginate (4% w/w) is prepared by dissolving 1.0 g alginate in 25 mL MQ-water. A homogenous aqueous solution is achieved after extensively stirring. Contrast agent (Au nanoparticles, d=16 nm) is prepared by reducing $HAuCl_4 \cdot 4H_2O$ with an appropriate reductive agent such as sodium acrylate, $NaBH_4$, citrate etc. to form spherical gold nanoparticles of predefined size depending on the method of reduction. Such particles can further be analyzed by methods known to people skilled in art (DLS, TEM, AFM, ICP-MS, UV-vis etc.). Such particles can furthermore be coated with e.g. a polymer such as MeO-PEG$_{5000}$-SH or the like to induce colloid stability and facilitate up-concentration of the nanoparticle suspension. A mixture of equally amount of contrast agent ($c_{Au}$=40 mg/mL) and gel-forming system (4% w/w) is prepared by mixing, resulting in a free flowing solution composed of sodium alginate (2% w/w) and sterically stabilized PEGylated gold nanoparticles ($c_{Au}$=20 mg/mL) which upon exposure to divalent cations such as $Ca^{2+}$ results in hydrogel formation.

In another embodiment, the gel-forming system comprises an alginate and chitosan co-formulation. Exemplary formulations comprise a gel-forming system comprising about 0.1 to about 10% w/w alginate and about 0.01 to about 5% w/w chitosan, such as 1 to about 5% w/w alginate and about 0.1 to about 1% w/w chitosan, in an aqueous solution buffered to a pH in the range of about 4 to about 7.0 For example, an alginate (2% w/w) and chitosan (0.125% w/w) mixture in MES-buffer (pH 6.1) is prepared. By mixing this solution with contrast agents such as Au nanoparticles coated with $PEG_{5000}$ (d=16 nm) to a final Au concentration of 1 mg/mL and subsequently exposure to divalent cations such as $Ca^{2+}$ hydrogel formation is achieved. Co-formulations composed of both alginate and chitosan may induce the ion sensitivity of the gel forming system, thus, forming hydrogels at lower salt concentrations.

In one embodiment the gel forming system comprises PEG-PPG-PEG, such as, e.g., Pluronic F127. Exemplary formulations comprise a gel-forming system comprising about 1 to about 60% w/w PEG-PPG-PEG, such as about 5 to about 50% w/w, about 20 to about 40% w/w, in aqueous solvent. For example, by mixing a (25% w/w) Pluronics F127 solution in $MQ-H_2O$ with contrast agents such as lipid coated Au nanoparticles (d=147.6 nm) to a final Au concentration of 0.16 mg/mL at rt a free flowing solution is obtained. By increasing the temperature to 37° C. a hydrogel encapsulating the lipid coated Au nanoparticles is achieved. Such a formulation may be used as an injectable thermo responsive hydrogel with encapsulated contrast agents.

In another embodiment, the gel-forming system comprises sucrose acetate isobutyrate (SAIB), optionally in a mixture with poly(D,L-lactic acid) (PLA) and/or poly(D,L-lactide-co-glycolide) acid (PGLA). Exemplary formulations comprise gel-forming systems comprising about 40 to about 95% w/w SAIB, such as about 50 to about 90%, about 50 to about 80% w/w, about 60 to about 80% w/w, about 70 to about 80%, about 60 to about 75% w/w, such as about 75% w/w in organic solvents such as EtOH, DMSO, NMP and the like. One example is a SAIB (about 75% w/w) and poly(D, L-lactic acid, $M_w$ 10-18 kDa) (about 5% w/w) mixture in anhydrous EtOH (about 20% w/w). For example, by mixing this solution with contrast agents such as Au nanoparticles coated with $PEG_{5000}$ (d=40 nm) in anhydrous EtOH to a final Au concentration of 10 mg/mL and subsequently exposure to an aqueous environment hydrogel formation is achieved. The release profile can be controlled, for example by varying the amount of PLA and/or PGLA and the organic solvent (e.g., EtOH) content in the formulation. For example, in some embodiments, the PLA is varied in the range from about 0.1% w/w to about 20% w/w, such as from about 0.5% w/w to about 9% w/w, about 1% to about 8% w/w, about 3% w/w to about 7% w/w or about 4% w/w to about 6% w/w. In some embodiments, the PGLA is varied in the range from about 0.1% w/w to about 20% w/w, such as from about 0.5% w/w to about 9% w/w, about 1% to about 8% w/w, about 3% w/w to about 7% w/w or about 4% w/w to about 6% w/w. In some embodiments, the combined PLA and PGLA content is varied in the range from about 0.1% w/w to about 20% w/w, such as from about 0.5% w/w to about 9% w/w, about 1% to about 8% w/w, about 3% w/w to about 7% w/w or about 4% w/w to about 6% w/w.

In one embodiment, the gel-forming system comprises poly(ethylene glycol-b-caprolactone) (PEG-PCL). Depending on the MW of the individual block polymers, exemplary formulations comprise gel-forming systems comprising about 5 to about 60% w/w, such as about 10 to about 50% w/w, about 15 to about 30% w/w, about 20 to about 40% w/w, or about 20 to about 25% w/w, such as about 20% or about 25% w/w PEG-PCL in an aqueous solution or buffer. One example is a $PEG_{750}$-$PCL_{2620}$ (20% w/w) in PBS-buffer (pH 7.4). For example, by mixing this solution with contrast agents such as Au nanoparticles coated with $PEG_{5000}$ (d=16 nm) in PBS-buffer to a final Au concentration of 1.5 mg/mL and subsequently heating to 37° C. hydrogel formation is achieved.

In one embodiment, the formulation of the invention comprises PEG-coated or PNIPAM-coated gold (Au) or bismuth (Bi) nanoparticles having a (number) average diameter of 1-500 nm, such as 5 to 100 nm, such as 10 to 50 nm, at a concentration of about 1 to about 30, such as about 5 to about 25, such as about 10 to about 20 mg/ml; and a gel-forming system comprising
  a) about 10 to about 50% w/w, about 15 to about 30% w/w, or about 20 to about 25% w/w PEG-PCL in an aqueous buffer; or
  b) about 60 to about 90, such as about 70 to about 85, such as about 72 to about 80% w/w SAIB; about 10 to about 25, such as about 15 to about 22, such as about 17 to about 20% w/w EtOH; and about 0 to about 10, such as about 3 to about 7, such as about 4 to about 6% w/w PLA and/or PGLA, wherein the SAIB, EtOH and PLA/PGLA together form 100% w/w.

The viscosity of any of the above formulations is such that it can be parenterally administered to a patient via a thin needle with no or minimal back-pressure. For example, a formulation of the invention can be injected with a back-pressure less than, for example, about 3 N, about 2 N or about 1 N via a hypodermal needle having a diameter corresponding to G17 or less, such as G19 or less, such as G21 or less, such as G23 or less, such as G25 or less, such as G25.

Use of the Formulations

The present invention also provides the formulation as defined hereinabove for use in X-ray imaging as a marker of specific tissue, such as computer tomography (CT), of the body of a mammal.

In one interesting embodiment, the formulation is parenterally administered to a predetermined location of the body of said mammal, and wherein an X-ray image of at least a part of the body of the mammal including the predetermined location is recorded.

A Kit Comprising the Formulation

The present invention further comprises a kit comprising a syringe, a hypodermal needle adapted to the open end of said syringe, and a formulation as defined hereinabove. In one embodiment, the formulation is held in the interior or said syringe.

The gel forming system may be provided as a lyophilized powder, a suspension or a solution. Different components may be provided in one or more individual vials or pre-mixed in the interior or said syringe. Exemplary different components include, but are not limited to, the gel-forming system and the solid particles, and the formulation and one or more initiators.

The syringe may consist of a single, a multiple barrel syringe (e.g. MEDMIX SYSTEMS AG) or a double champer syringe (e.g. Debiotech S. A.) and the like, but not limited to those. Multiple barrel syringes and double champer syringes and the like may be useful for e.g. two components formulations were one component is a mixture of the gel forming system and the contrast agent(s) and the other component is an initiator or salt suspension of e.g. $Ca^{2+}$ in the case there the gel forming system is based on alginate.

The needle of the syringe can, in some embodiments, be one suitable for fine-needle biopsies. Non-limiting examples of syringes and needles for such embodiments are described in U.S. Pat. No. 7,871,383, U.S. patent publication No. 20040162505, and references cited therein. Such syringes and needles can advantageously be used in procedures where a biopsy of a tissue is to be taken in conjunction with imaging of the same, using a formulation of the invention. Preferably, the kit has a shelf-life of at least 6 months, such as at least 12 months when stored at, e.g., room temperature (typically 18 to 25° C.) or lower temperatures, such as, e.g., 2 to 10° C., such as about 5° C. The shelf-life can, for example, be determined as the period wherein the kit can be stored at 25° C., at 80% RH and 1 atm. pressure, and where the viscosity is kept within ±5% of the initial viscosity.

A Method of Recording an X-Ray Image of a Body of Mammal

The present invention also provides a method of recording an image, optionally an X-ray image, of the body of a mammal, comprising the steps of:
(a) providing a formulation comprising a plurality of solid in-organic particles and an organic gel-forming system, wherein said solid in-organic particles have a (number) average diameter of 1-500 nm and comprise a detectable compound, optionally detectable by X-ray imaging;
(b) administering the formulation to a subject, and
(c) recording images, optionally X-ray such as Computed Tomography (CT)-images.

In one embodiment, the method is for joint radiotherapy and X-ray imaging of a target tissue in an individual, wherein the images in step (c) provides a definition of the target tissue, and further comprises the step of:
(d) using the definition of the target tissue obtained in c) to direct external beam radiotherapy to the target tissue.

In one embodiment, the method is for directing local administration of a pharmaceutically active agent to a target tissue in an individual, wherein the images in step (c) provides a definition of the target tissue, and further comprises the step of:
(d) using the definition of the target tissue obtained in c) to direct local administration of a pharmaceutically active agent to the target tissue.

In one embodiment, the formulation comprises the pharmaceutically active agent, optionally as described elsewhere herein.

The target tissue is typically one that comprises undesirably growing cells. In one embodiment, the undesirably growing cells are tumor cells, such as malignant cells, and the individual is suffering from or at risk for cancer. In a particular embodiment, the undesirable growth of cells is associated with lung cancer, prostate cancer, cervix or ovarian cancer. Other types of conditions or diseases associated with undesirable cell growth include extra uterine (ectopic) pregnancy, benign tumours in brain, such as benign tumours located closely to the optical nerve, glandule with overproduction of hormone, such as for example hypothalamus, bone and cartilage in relation with nerve compression, blood cells which may be killed prior to transplantation, conditions associated with large tonsils such as acute tonsillitis or adenoiditis, obstructive sleep apnoea, nasal airway obstruction, snoring, or peritonsillar abscess or hyperplasic or angiogenic eye disorders.

In one embodiment, the formulation provided in (a) is provided as part of a kit according to one or more embodiments described above. In embodiments where the formulation is provided as a lyophilized powder, step (a) may further comprise dissolving the powder in a liquid suitable for administration to a patient. In embodiments where the gel-forming system and the solid particles are provided in separate vials, step (a) may further comprise the step of mixing the two.

In embodiments where the gel-forming system is one that gels upon the addition of an initiator, the administration step (a) or (b) may further comprise mixing with an initiator.

The formulation according to the present invention may be administered parenterally, such as by intravenous, intramuscular, intraspinal, subcutaneous, intraarterial, intracardiac, intraosseous, intradermal, intracisternal, intrathecal, intracerebral, transdermal, transmucosal, inhalational, epidural, sublingual, intravitreal, intranasal, intrarectal, intravaginal or intraperitoneal administration. The parental administration may be performed by, e.g., infusion or injection. Typically, the formulation is administered into, or adjacent to, a predetermined location, such as a target tissue, optionally in conjunction with a biopsy of the target tissue, and optionally in conjunction with local administration of a pharmaceutically active agent.

The amount of formulation to administer to the mammal or individual in step (c) can be determined by one of skill in the art, taking into consideration the nature of the investigation and the size of the area to be imaged. Typically, at least 100 µL formulation is administered. In various specific embodiments, the method comprises administration of between 100 µL and 20 mL, such as between 200 µL and 10 mL, such as between 200 µL and 2 mL.

In step (c), an X-ray image is typically recorded of at least a part of the body of the mammal including the predetermined location. In particular embodiments, steps (c) and (d) may be performed simultaneously, so that image-recording and execution of radiotherapeutic treatment or local administration of a pharmaceutically active agent is integrated and performed sequentially or simultaneously.

Use of the Formulation as a Tissue Sealant

The present invention also provides the formulation as defined hereinabove for use as a tissue sealant, e.g. for needle canals formed by biopsy in conjunction with an imaging procedure according to the invention.

The tissue sealant may include an effective amount of a hemostatic agent, e.g. an agent selected from coagulation factors, coagulation initiators, platelet activators, vasoconstrictors and fibrinolysis inhibitors, e.g. epinephrine, adrenochrome, collagens, thrombin, fibrin, fibrinogen, oxidized cellulose and chitosan.

EXAMPLES

Figure 6:
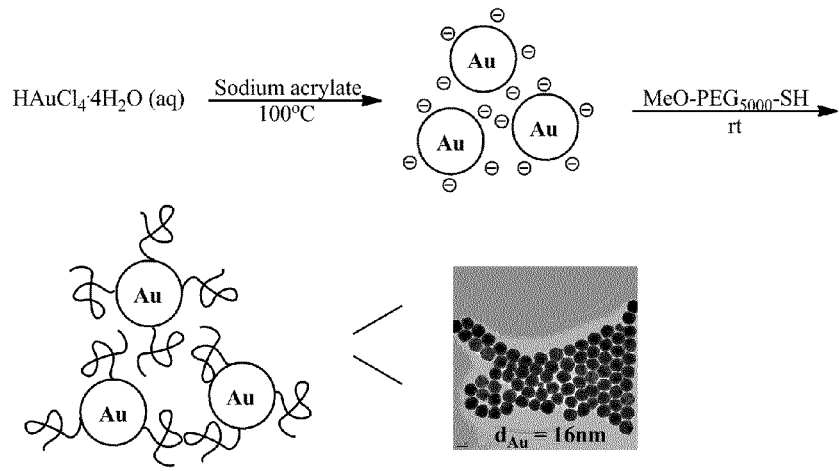
FIG. 6 illustrates an approach to encapsulate PEGylated Au nanoparticles in $Ca^{2+}$ sensitive alginate hydrogels.
Figure 6:
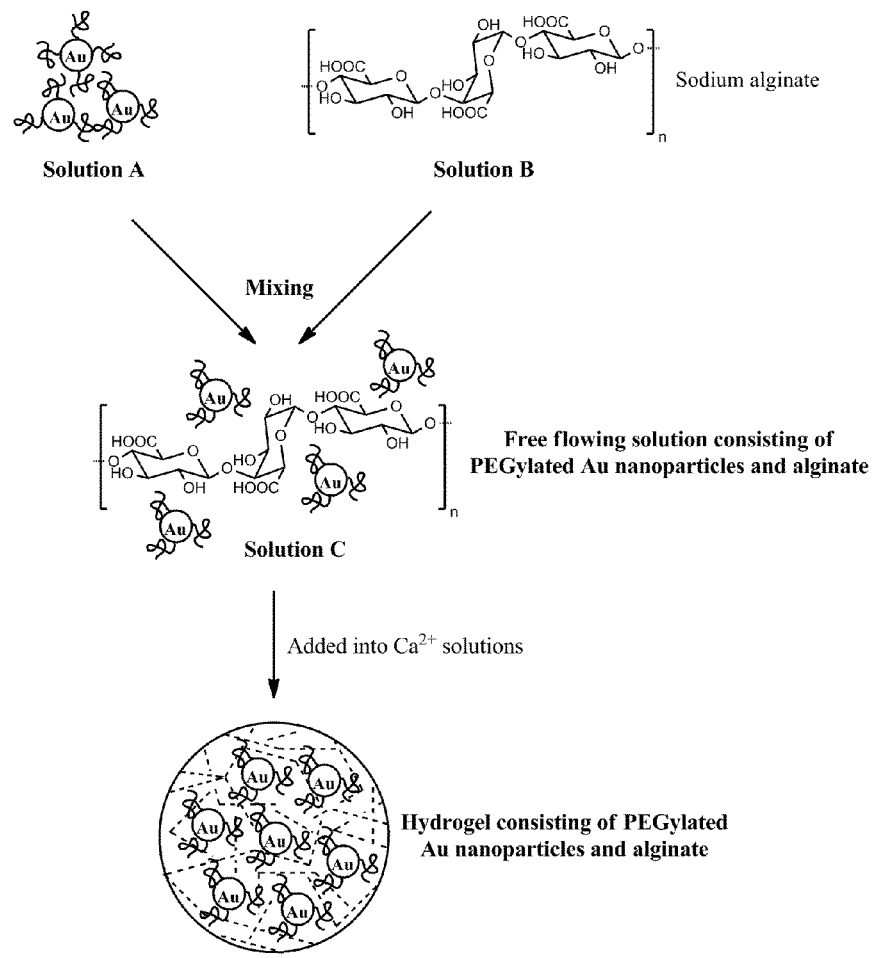

Example 1—PEGylated Au Nanoparticles Encapsulated in Ion Sensitive Alginate Based Hydrogels (FIG. 6)

Materials

Sodium alginate, $CaCl_2$ and sodium acrylate were purchased from Sigma-Aldrich (Brøndby, Denmark). MeO-$PEG_{5000}$-SH was purchased from Rapp Polymere GmbH (Tuebingen, Germany) and $HAuCl_4.4H_2O$ was purchased from Wako Chemicals GmbH (Neuss, Germany).

Au Nanoparticle Formation

Solid Au nanoparticles were prepared by reducing $HAuCl_4.4H_2O$ with sodium acrylate. All glassware was cleaned with aqua regia prior to use. Aqueous $HAuCl_4.4H_2O$ (1 mM, 25 mL) was heated to reflux on a oil bath for 10 min after which warm (60° C.) sodium acrylate (80 mM, 7.5 mL) was added quickly and the solution kept at 100° C. for 30 min. The formed acrylate stabilized Au nanoparticles were analyzed by UV-vis ($\lambda_{max}$=527 nm), DLS (30.5 nm±0.8 nm), ζ-potential (−41.9±2.1 mV). PEGylation of the acrylate stabilized Au nanoparticles (25 mL) was achieved by adding aqueous MeO-$PEG_{5000}$-SH (0.9 mM, 5 mL) at rt under stirring overnight. The particles were purified by centrifugation (9.500 RPM, 4×20 min) and extensive washed with MQ-H$_2$O (4×30 mL). The PEGylated Au nanoparticles were analyzed by UV-vis ($\lambda_{max}$=528 nm), DLS (57.2 nm±0.4 nm), ζ-potential (−17.6±0.4 mV) and TEM (16 nm). The PEGylated Au nanoparticles were up concentrated by centrifugation and the final concentration determined by inductively coupled plasma mass spectroscopy (ICP-MS).

Alginate Hydrogel Formation

An aqueous free flowing solution of sodium alginate (2% w/w) and sterically stabilized PEGylated gold nanoparticles ($c_{Au}$=20 mg/mL) was prepared by mixing the two components under stirring at rt. The obtained solution was added drop wise to vials containing CaCl$_2$-solutions with a Ca$^{2+}$ concentration of 250 mM, 125 mM, 50 mM, 25 mM, 5 mM, 2.5 mM and 1 mM, respectively. Gel formation was observed for all of the concentrations except 1 mM and 2.5 mM Ca$^{2+}$ with no visible sign of leakage of the sterically stabilized PEGylated gold nanoparticles. The experiment showed that alginate still form gels in the presence of gold nanoparticles with a concentration of 20 mg/mL. The gel formed was a dark brown pellet and the droplet size determined the size of the capsules being formed.

Example 2—PEGylated Au Nanoparticles Encapsulated in Ion Sensitive Chitosan/Alginate Based Hydrogels Materials Sodium alginate, CaCl$_2$, sodium acrylate and chitosan were purchased from Sigma-Aldrich (Brøndby, Denmark). MeO-PEG$_{5000}$-SH was purchased from Rapp Polymere GmbH (Tuebingen, Germany) and HAuCl$_4$.4H$_2$O was purchased from Wako Chemicals GmbH (Neuss, Germany).

Au Nanoparticle Formation

PEGylated Au nanoparticles were prepared as described in Example 1.

Chitosan/Alginate Hydrogel Formation In Vitro

An aqueous free flowing solution of sodium alginate (2% w/w), chitosan (0.125% w/w) and sterically stabilized PEGylated Au nanoparticles ($c_{Au}$=1 mg/mL) was prepared by mixing the three components under stirring at rt. The obtained solution was added drop wise to vials containing CaCl$_2$-solutions with a Ca$^{2+}$ concentration of 20 mM, 10 mM and 5 mM—all adjusted to physiological osmolarity with NaCl. Gel formation was observed for all of the concentrations with no visible sign of leakage of the sterically stabilized PEGylated Au nanoparticles. The experiment showed that chitosan/alginate still form gels in the presence of gold nanoparticles with a concentration of 1 mg/mL. The gel formed was more condensed compared to gels only consisting of alginate and remained its morphology up to 1 month.

Figure 7:
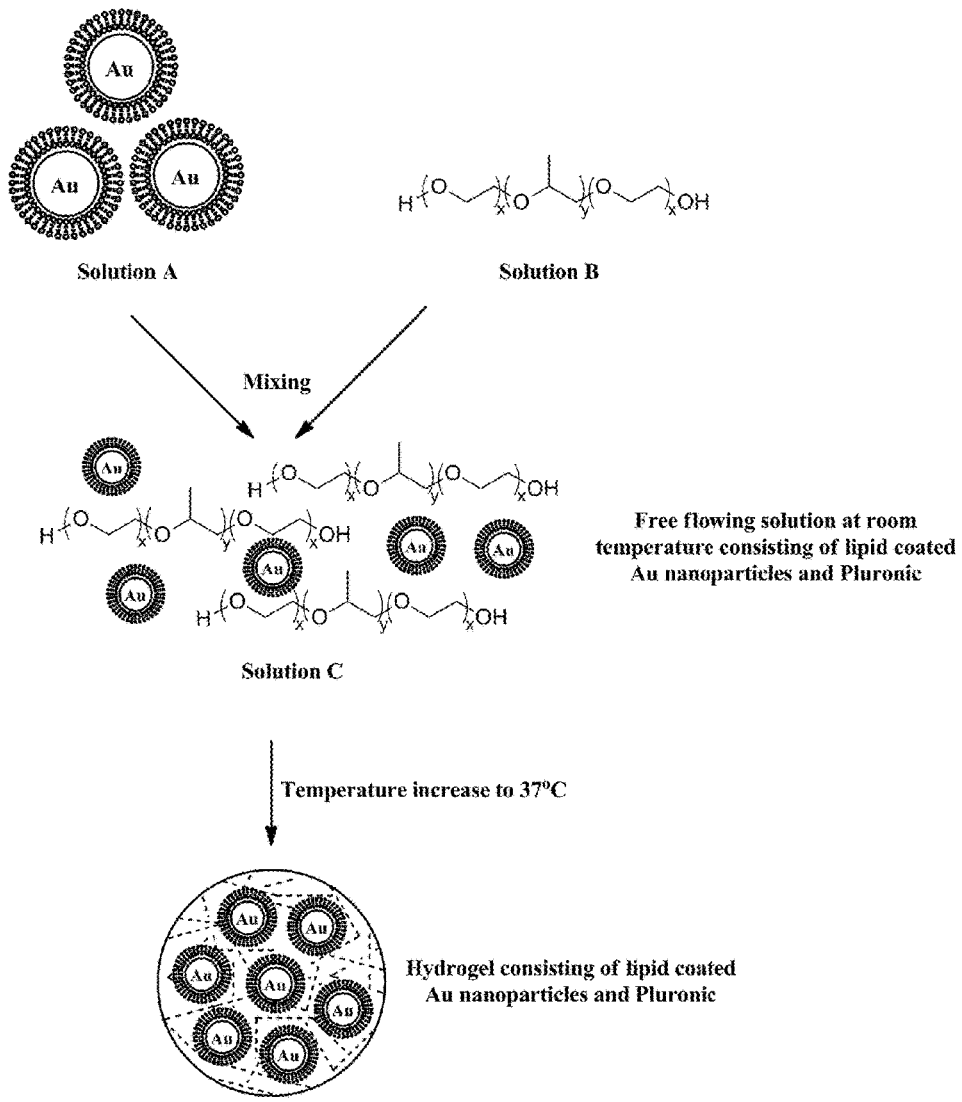
FIG. 7 illustrates an approach to encapsulate lipid coated Au nanoparticles in thermo sensitive Pluronic based hydrogels.

Example 3—Lipid Coated Au Nanoparticles Encapsulated in Thermo Sensitive Pluronic Based Hydrogels (FIG. 7)

Materials

Pluronic F127, NaBH$_4$, cysteamine and cellulose based dialysis tubing (MWCO 11.011 Da) were purchased from Sigma-Aldrich (Brøndby, Denmark). 1-palmitoyl-2-oleoyl-sn-glycero-3-phosphocholine (POPC) and 1-palmitoyl-2-oleoyl-sn-glycero-3-phospho(1'-rac-glycerol) (POPG) were purchased from Avanti Polar Lipids (Birmingham, Ala., USA) and HAuCl$_4$.3H$_2$O was purchased from Wako Chemicals GmbH (Neuss, Germany).

Au Nanoparticle Formation

Solid Au nanoparticles were prepared by reducing HAuCl$_4$.3H$_2$O with sodium borohydride. All glassware was cleaned with aqua regia prior to use. Cysteamine (0.31 mM, 400 µL) was added to aqueous HAuCl$_4$.3H$_2$O (1.57 mM, 40 mL) at rt. The solution was protected from sunlight and sodium borohydride (10 mM, 10 µL) was added. After 12 min, the reaction suspension was transferred to a dialysis tube (MWCO 11.011 Da) and dialyzed against MQ-H$_2$O (3×2,000 mL) for 24 h. The formed cysteamine stabilized Au nanoparticles were analyzed by UV-vis ($\lambda_{max}$=530 nm), DLS (51.4 nm±0.3 nm), ζ-potential (+26.5±1.4 mV). An aliquot of dialyzed cysteamine stabilized Au nanoparticles (8 mL) were transferred to a vial containing; POPC: POPG (70:30% w/w) (4.1 mg). The lipid film was hydrated by extensive vortexing for 30 min at rt. Excess of lipid material was removed by centrifugation (5,000 RPM, 10 min). The supernatant was carefully removed and the lipid coated particles re-suspended in MQ-H$_2$O (1 mL). The lipid coated Au nanoparticles was analyzed by DLS (147.6 nm±19.9 nm) and ζ-potential (−86.8±1.02 mV). Smaller lipid coated Au nanoparticles could be obtained by additional sonication after removal of excess lipid material. The lipid coated Au nanoparticles were stored at 4° C.

Pluronic Hydrogel Formation In Vitro

An aqueous free flowing solution of Pluronic F127 (25% w/w) and lipid coated gold nanoparticles ($c_{Au}$=0.16 mg/mL) in MQ-H$_2$O was prepared by mixing the two components under stirring at rt. Incubation of the gel forming components at 37° C. resulted in gel-formation within one minute. The gel formation was found to be reversible, thus, a free flowing solution could be obtained at 4° C.

Figure 8:
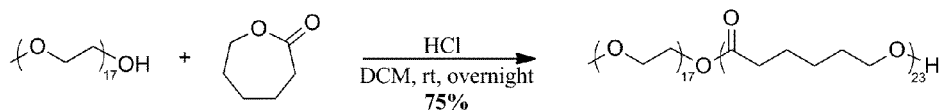
FIG. 8 illustrates an approach to encapsulate PEGylated Au nanoparticles in thermo sensitive poly(ethylene glycol-b-caprolactone) (PEG-PCL) based hydrogels.
Figure 8:
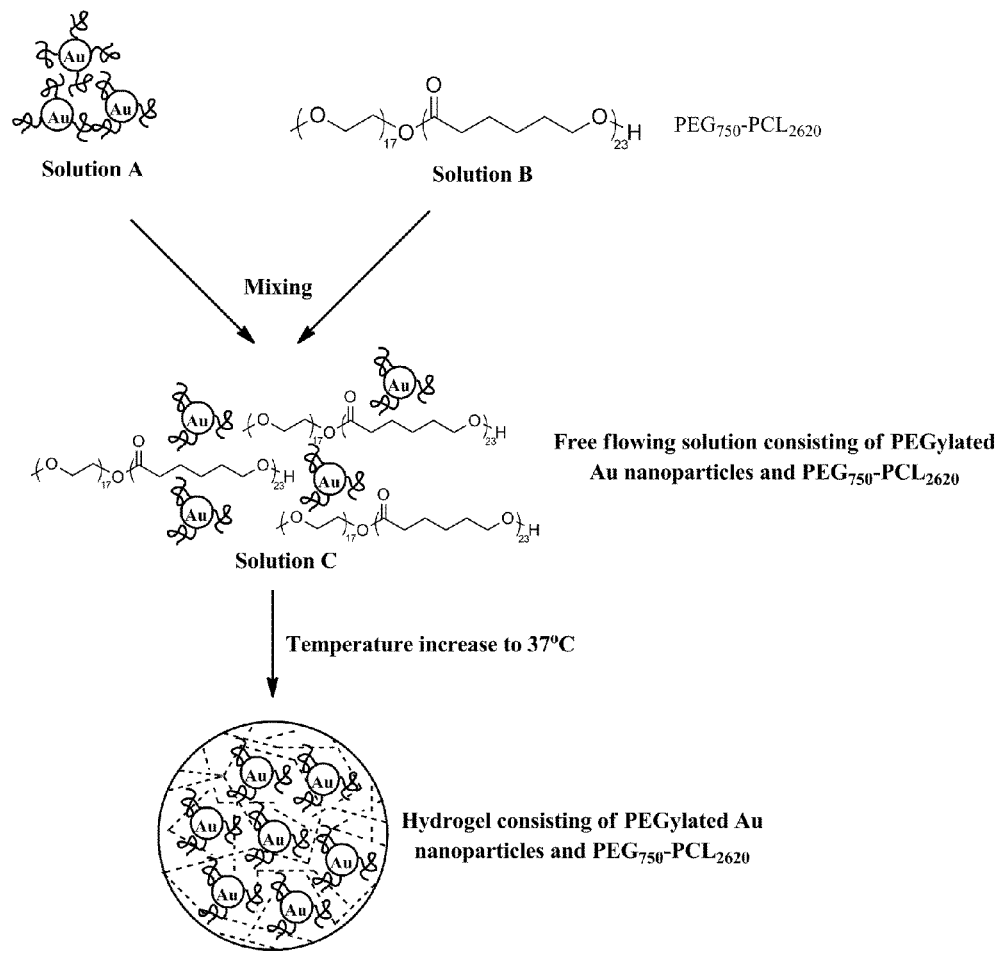

Example 4—PEGylated Au Nanoparticles Encapsulated in Thermo Sensitive PCL-PEG Based Hydrogels (FIG. 8)

Materials

ε-Caprolactone, HCl·dioxane (4M), MeO-PEG$_{750}$-OH and sodium acrylate were purchased from Sigma-Aldrich (Brøndby, Denmark). MeO-PEG$_{5000}$-SH was purchased from Rapp Polymere GmbH (Tuebingen, Germany) and HAuCl$_4$.4H$_2$O was purchased from Wako Chemicals GmbH (Neuss, Germany).

Au Nanoparticle Formation

PEGylated Au nanoparticles were prepared as described in Example 1.

Synthesis of PEG$_{750}$-PCL$_{2620}$ Diblock Co-Polymer

MeO-PEG$_{750}$-OH (600 mg, 0.80 mmol) was added to a flame dried flask and residual water was removed by azeotrope distillation with dry toluene (2×15 mL). The dried PEG was dissolved in dry CH$_2$Cl$_2$ (7 mL) and ε-caprolactone (1.55 g, 13.2 mmol) and HCl·dioxane (400 µL, 4 M) were added to the stirred solution under N$_2$-atmosphere. The solution was stirred overnight at rt after which the solvent was removed under vacuo. The residual solid was dissolved in CH$_2$Cl$_2$ (2 mL) and precipitated by addition into ice cold n-hexane (100 mL) under stirring. The product was filtrated and washed extensively with cold n-hexane. The remaining solid were dissolved in DCM and the solvent removed under vacuo. The final product was lyophilized from a mixture of water and MeCN to give the title compound as a fluffy white powder (2.03 g, 75%). $^1$H-NMR (300 MHz, CDCl$_3$): δ 4.18 (—CH$_2$CH$_2$O—COCH$_2$CH$_2$CH$_2$CH$_2$CO—), 3.95 (—OCH$_2$CH$_2$CH$_2$CH$_2$CO—), 3.58 (—OCH$_2$CH$_2$—), 3.24 (CH$_3$O—), 2.24 (—COCH$_2$CH$_2$CH$_2$—CH$_2$CO—), 1.59 (—COCH$_2$CH$_2$CH$_2$CH$_2$CH$_2$CO—), 1.26

(—COCH$_2$CH$_2$CH$_2$CH$_2$CH$_2$CO—). The ethylene peak of the ethylene glycol (—OCH$_2$CH$_2$—) unit at 3.58 ppm and the methylene peak of the caprolactone (—COCH$_2$CH$_2$CH$_2$CH$_2$CH$_2$CO—) unit at 2.24 ppm in the $^1$H-NMR spectra were used for the determination of number average molecular weight of the PEG-PCL diblock copolymer.

PEG$_{750}$-PCL$_{2620}$ Hydrogel Formation In Vitro

An aqueous free flowing solution of PEG$_{750}$-PCL$_{2620}$ (20% w/w) was prepared by suspending PEG$_{750}$-PCL$_{2620}$ (85.5 mg) in PBS-buffer (342 µL) and heating the solution to 80° C. on an oil bath for 5 min after which it was allowed to cool to room temperature to form a slightly viscous free flowing homogenous solution. Sterically stabilized PEGylated Au nanoparticles ($c_{Au, final}$=1.5 mg/mL) was added by mixing the two components at room temperature. Incubation of the gel forming components at 37° C. in a water bath resulted in gel-formation within five minutes. Gel formation was found to be reversible, thus, a free flowing solution could be obtained upon lowering the temperature.

Figure 9:
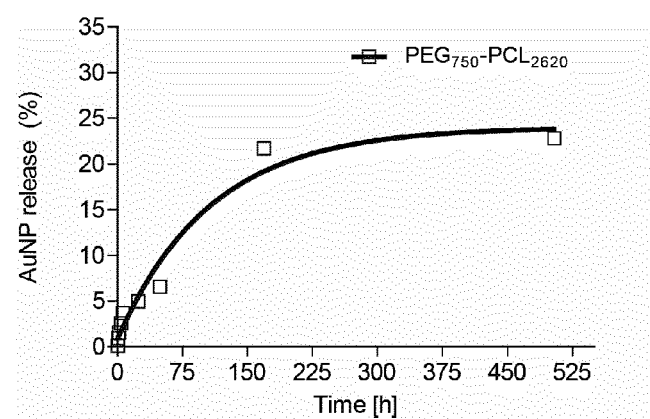
FIG. 9 illustrates the in vitro release profile for a $PEG_{750}$-$PCL_{2620}$ hydrogel with 2.5 mg AuNP/mL in in PBS-buffer at 37° C.

In Vitro Release of PEGylated Au Nanoparticles from PEG$_{750}$-PCL$_{2620}$ (20% w/w) Hydrogels A PEG$_{750}$-PCL$_{2620}$ (20% w/w)+2.5 mg Au/mL hydrogel solution was prepared as previously described. The PEG$_{750}$-PCL$_{2620}$ (20% w/w)+2.5 mg Au/mL hydrogel solution (250 µL) was transferred into a 2.0 mL glass vial and incubated at 37° C. overnight. Warm PBS-buffer (1500 uL, 37° C.) was carefully added to the gel and aliquots (750 µL) were removed as a function of time and replaced with fresh warm PBS-buffer (750 µL). The amount of released AuNPs was measured by correlating the UV-vis absorbance at 528 nm with a standard curve based on Au-standards of known concentration. A plateau of approximately 20% leakage of PEGylated AuNPs was observed within 7 days (FIG. 9).

Figure 10:
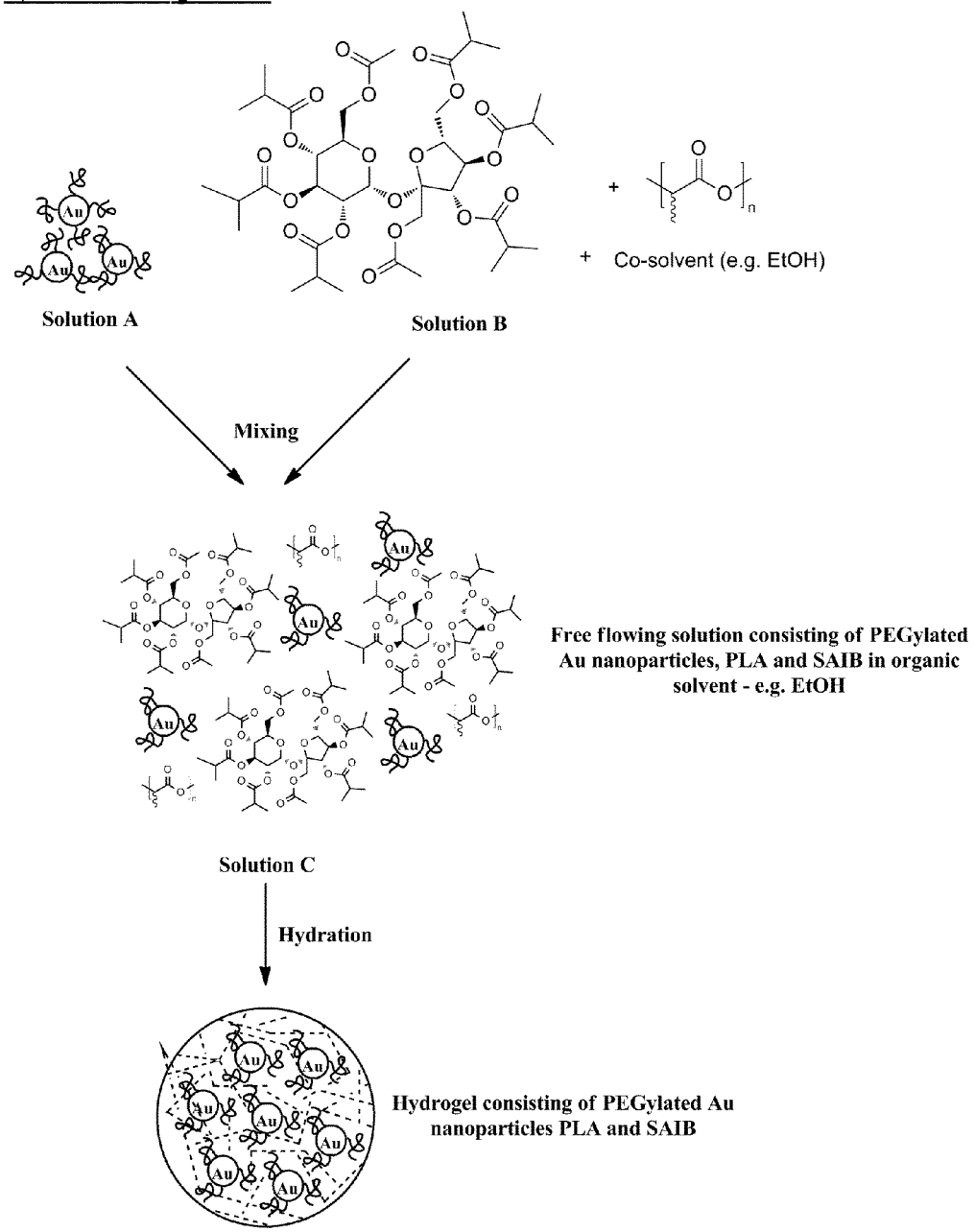
FIG. 10 illustrates an approach to encapsulate PEGylated Au nanoparticles in hydration sensitive SAIB based hydrogels.

Example 5—PEGylated Au Nanoparticles Encapsulated in Hydration Sensitive Sucrose Acetate Isobutyrate (SAIB) Based Hydrogels (FIG. 10)

Materials

SAIB, trisodium citrate dihydrate, poly(D,L-lactic acid) (PLA) ($M_w$ 10-18 kDa), Poly(D,L-lactide-co-glycolide) acid terminated (PLGA) (lactide:glycolide 75:25, $M_w$ 4-15 kDa) and anhydrous EtOH were purchased from Sigma-Aldrich (Brøndby, Denmark). MeO-PEG$_{5000}$-SH was purchased from Rapp Polymere GmbH (Tuebingen, Germany) and HAuCl$_4$.3H$_2$O was purchased from Wako Chemicals GmbH (Neuss, Germany). Thiol terminated Poly(N-isopropyl acrylamide) (PNIPAM) ($M_w$ 3.5 kDa) was purchased from Polymer Source Inc. (Dorval, Canada).

Au Nanoparticle Formation—PEGylated AuNPs (PEG$_{5000}$)

Solid Au nanoparticles were prepared by reducing HAuCl$_4$.3H$_2$O with trisodium citrate dihydrate. All glassware was cleaned with aqua regia prior to use. Aqueous HAuCl$_4$.3H$_2$O (1 mM, 50 mL) was heated to reflux on a oil bath for 10 min under vigorous stirring after which trisodium citrate dihydrate (38.8 mM, 5.0 mL) was added quickly and the solution refluxed for 15 min. The formed citrate stabilized Au seeds were analyzed by UV-vis ($\lambda_{max}$=517 nm), DLS (41.8 nm±0.5 nm). The obtained AuNP seeds (20.0 mL) were used directly in the next step and added to a refluxing solution of HAuCl$_4$.3H$_2$O (2500 mL, 0.30 mM) under vigorous stirring. Subsequently, trisodium citrate dihydrate (11.2 mL, 38.8 mM) was added and the mixture refluxed for 30 min after which additional trisodium citrate dihydrate (100 mL, 38.8 mM) was added as stabilizer and the mixture heated for one hour. The formed citrate stabilized Au nanoparticles were analyzed by UV-vis ($\lambda_{max}$=534 nm), DLS (51.8 nm±0.8 nm). PEGylation of the citrate stabilized Au nanoparticles (2600 mL) was achieved by adding MeO-PEG$_{5000}$-SH (75 mg, 15 µmol) at rt under stirring overnight. The particles were purified by centrifugation (9.500 RPM, 4×10 min) and extensive washed with MQ-H$_2$O (4×30 mL). The PEGylated Au nanoparticles were analyzed by UV-vis ($\lambda_{max}$=537 nm), DLS (57.8 nm±0.8 nm) and ζ-potential (−23.4±3.5 mV). The PEGylated Au nanoparticles were up concentrated by centrifugation and the final concentration determined by inductively coupled plasma atomic emission spectroscopy (ICP-AES).

Au Nanoparticle Formation—PNIPAM Coated AuNPs (PNIPAM$_{3500}$)

Solid Au nanoparticles were prepared by reducing HAuCl$_4$.3H$_2$O with trisodium citrate dihydrate. All glassware was cleaned with aqua regia prior to use. Aqueous HAuCl$_4$.3H$_2$O (1 mM, 50 mL) was heated to reflux on a oil bath for 10 min under vigorous stirring after which trisodium citrate dihydrate (38.8 mM, 5.0 mL) was added quickly and the solution refluxed for 15 min. The formed citrate stabilized Au seeds were analyzed by UV-vis ($\lambda_{max}$=519 nm), DLS (15.1 nm, number based). The obtained AuNP seeds (20.0 mL) were used directly in the next step and added to a refluxing solution of HAuCl$_4$.3H$_2$O (2500 mL, 0.30 mM) under vigorous stirring. Subsequently, trisodium citrate dihydrate (11.2 mL, 38.8 mM) was added and the mixture refluxed for 30 min after which additional trisodium citrate dihydrate (100 mL, 38.8 mM) was added as stabilizer and the mixture heated for one hour. The formed citrate stabilized Au nanoparticles were analyzed by UV-vis ($\lambda_{max}$=537 nm), DLS (42.7 nm±0.7 nm). PNIPAM coating of the citrate stabilized Au nanoparticles (2600 mL) was achieved by adding SH-PNIPAM$_{3500}$ (52.6 mg, 15 µmol) at rt under stirring overnight. The particles were purified by centrifugation (9.500 RPM, 4×15 min) and extensive washed with MQ-H$_2$O (3×30 mL). The PEGylated Au nanoparticles were analyzed by UV-vis ($\lambda_{max}$=539 nm), DLS (55.6 nm±0.3 nm) and ζ-potential (−33.8±1.7 mV). The PEGylated Au nanoparticles were up concentrated by centrifugation and the final concentration determined by inductively coupled plasma atomic emission spectroscopy (ICP-AES).

SAIB/EtOH/PLA Hydrogel Formation In Vitro—Exp A; Effect of PLA in Gel

SAIB (2.50 g, 90 w % in EtOH) and PLA (150 mg) were mixed and homogenized by a ball homogenizer (frequency 30 s$^{-1}$, 30 min) to give a clear homogenous solution. PEGylated AuNPs (306 µL, 30 mg Au (98 mg Au/mL by ICP-AES)) were transferred into EtOH by centrifugation (10.000 RPM, 15 min). The supernatant was discarded and replaced three times with EtOH (3×1 mL), the final volume adjusted to 434 µL and added to the SAIB/PLA mixture to give a final nanogel forming matrix composed of SAIB/EtOH/PLA (75:20:5) with 10 mg/mL PEGylated AuNPs.

Figure 11:
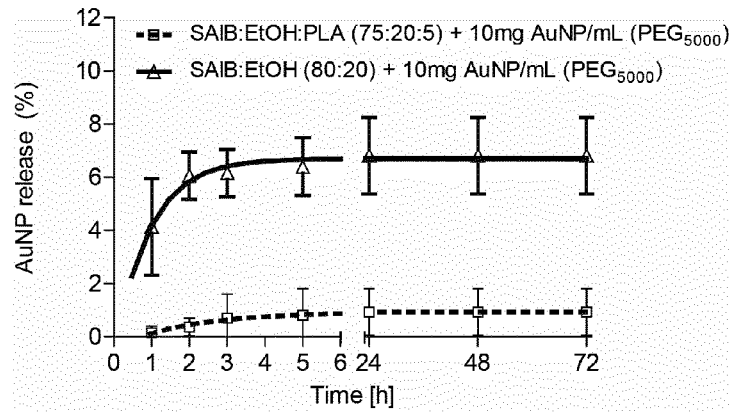
FIG. 11 illustrates the in vitro release profile for SAIB/EtOH/PLA (75:20:5) and SAIB/EtOH/(80:20) hydrogels both with 10 mg AuNP/mL in PBS-buffer at 37° C. Open squares; SAIB/EtOH/PLA (75:20:5), open triangles; SAIB/EtOH/(80:20).

SAIB/EtOH/PLA (75:20:5) with 10 mg/mL PEGylated AuNPs (200 µL) were added to a glass vials containing PBS-buffer (10.0 mL, 37° C.) and small aliquots (1.00 mL) were removed as a function of time and replaced with fresh PBS-buffer. The amount of released AuNPs was measured by correlating the UV-vis absorbance at 539 nm with a standard curve based on Au-standards of known concentration. Less than 2% leakage of PEGylated AuNPs was observed within 3 days. Formulations without addition of 5 w % PLA resulted in approx. 7% leakage within the same time frame (FIG. 11).

SAIB/EtOH/PLA Hydrogel Formation In Vitro—Exp B; Effect of Amount of AuNP in Gel SAIB (0.83 g, 90 w % in EtOH) and PLA (50 mg) were mixed and homogenized by a ball homogenizer (frequency 30 s$^{-1}$, 30 min) to give a clear homogenous solution. PEGylated AuNPs (363 µL, 30 mg Au (83 mg Au/mL by ICP-AES)) were transferred into EtOH by centrifugation (10.000 RPM, 15 min). The supernatant was discarded and replaced three times with EtOH (3×1 mL), the final volume adjusted to 148 µL and added to the SAIB/PLA mixture to give a final nanogel forming matrix composed of SAIB/EtOH/PLA (75:20:5) with 30 mg/mL PEGylated AuNPs.

Figure 12:
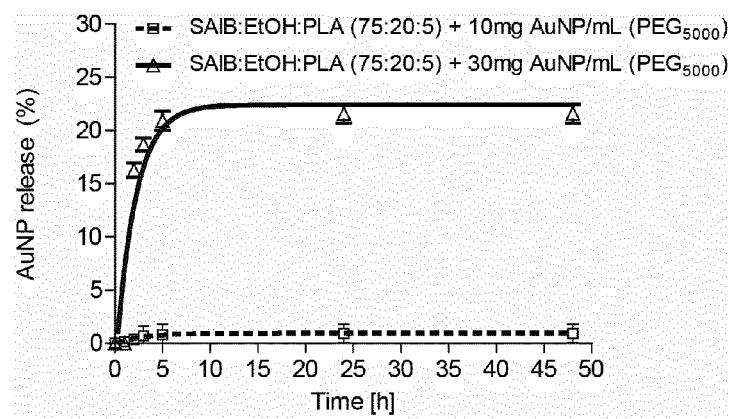
FIG. 12 illustrates the in vitro release profile for SAIB/EtOH/PLA (75:20:5)+10 mg AuNP/mL and SAIB/EtOH/PLA (75:20:5)+30 mg AuNP/mL hydrogels in PBS-buffer at 37° C. Open squares; SAIB/EtOH/PLA (75:20:5)+10 mg AuNP/mL, open triangles; SAIB/EtOH/PLA (75:20:5)+30 mg AuNP/mL.

SAIB/EtOH/PLA (75:20:5) with 30 mg/mL PEGylated AuNPs (200 µL) were added to a glass vials containing PBS-buffer (10.0 mL, 37° C.) and small aliquots (1.00 mL) were removed as a function of time and replaced with fresh PBS-buffer. The amount of released AuNPs was measured by correlating the UV-vis absorbance at 539 nm with a standard curve based on Au-standards of known concentration. Less than 2% leakage of PEGylated AuNPs from SAIB-gels with 10 mg AuNP/mL was observed within 2 days. Formulations with 30 mg AuNP/mL resulted in approx. 20% leakage within the same time frame (FIG. 12).

SAIB/EtOH/PLA Hydrogel Formation In Vitro—Exp C; Effect of Amount of EtOH in Gel SAIB (287 mg, 90 w % in EtOH) and PLA (16.7 mg) were mixed and homogenized by a ball homogenizer (frequency 30 s$^{-1}$, 45 min) to give a clear homogenous solution. PEGylated AuNPs (120 µL, 10 mg Au (83 mg Au/mL by ICP-AES)) were transferred into EtOH by centrifugation (13.400 RPM, 5 min). The supernatant was discarded and replaced three times with EtOH (3×1 mL), the final volume adjusted to 37.6 µL and added to the SAIB/PLA mixture to give a final nanogel forming matrix composed of SAIB/EtOH/PLA (77.5:17.5:5) with 30 mg/mL PEGylated AuNPs.

Figure 13:
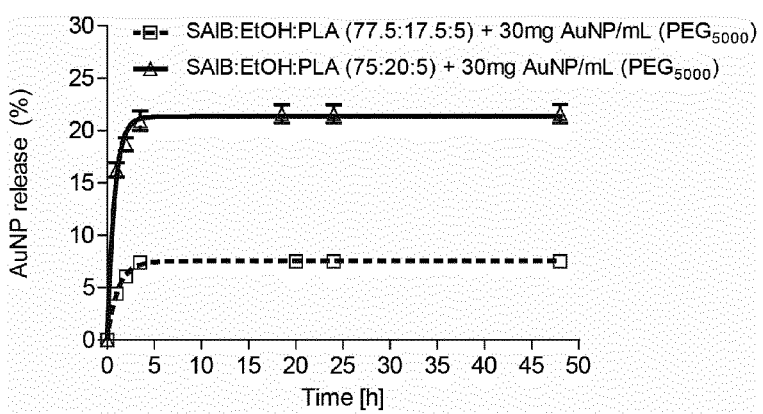
FIG. 13 illustrates the in vitro release profile for SAIB/EtOH/PLA (77.5:17.5:5)+30 mg AuNP/mL and SAIB/EtOH/PLA (75:20:5)+30 mg AuNP/mL hydrogels in PBS-buffer at 37° C. Open squares; SAIB/EtOH/PLA (77.5:17.5:5)+30 mg AuNP/mL, open triangles; SAIB/EtOH/PLA (75:20:5)+30 mg AuNP/mL.

SAIB/EtOH/PLA (77.5:17.5:5) with 30 mg/mL PEGylated AuNPs (200 µL) were added to a glass vials containing PBS-buffer (10.0 mL, 37° C.) and small aliquots (1.00 mL) were removed as a function of time and replaced with fresh PBS-buffer. The amount of released AuNPs was measured by correlating the UV-vis absorbance at 539 nm with a standard curve based on Au-standards of known concentration. Reduction of the EtOH content to 17.5% w/w resulted in less than 7% leakage of PEGylated AuNPs within 2 days. Formulations with 20% w/w EtOH resulted in approx. 20% leakage within the same time frame (FIG. 13).

SAIB/EtOH/PLGA Hydrogel Formation In Vitro—Exp D; Effect of Substitution of PLA with PLGA in Gel SAIB (278 mg, 90 w % in EtOH) and PLGA (16.7 mg) were mixed and homogenized by a ball homogenizer (frequency 30 s$^{-1}$, 45 min) to give a clear homogenous solution. PEGylated AuNPs (120 µL, 10 mg Au (83 mg Au/mL by ICP-AES)) were transferred into EtOH by centrifugation (13.400 RPM, 5 min). The supernatant was discarded and replaced three times with EtOH (3×1 mL), the final volume adjusted to 49.2 µL and added to the SAIB/PLGA mixture to give a final nanogel forming matrix composed of SAIB/EtOH/PLGA (75:20:5) with 30 mg/mL PEGylated AuNPs.

Figure 14:
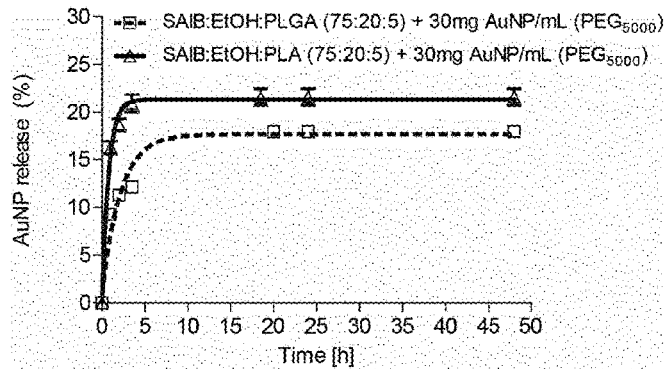
FIG. 14 illustrates the in vitro release profile for SAIB/EtOH/PLGA (75:20:5)+30 mg AuNP/mL and SAIB/EtOH/PLA (75:20:5)+30 mg AuNP/mL hydrogels in PBS-buffer at 37° C. Open squares; SAIB/EtOH/PLGA (75:20:5)+30 mg AuNP/mL, open triangles; SAIB/EtOH/PLA (75:20:5)+30 mg AuNP/mL.

SAIB/EtOH/PLGA (75:20:5) with 30 mg/mL PEGylated AuNPs (200 µL) were added to a glass vials containing PBS-buffer (10.0 mL, 37° C.) and small aliquots (1.00 mL) were removed as a function of time and replaced with fresh PBS-buffer. The amount of released AuNPs was measured by correlating the UV-vis absorbance at 539 nm with a standard curve based on Au-standards of known concentration. A small reduction of AuNP leakage (2%) was observed by substituting PLA within a time frame of 2 days (FIG. 14).

SAIB/EtOH/PLA Hydrogel Formation In Vitro—Exp E; Effect of Changing AuNP Coating from PEG$_{5000}$ to PNIPAM$_{3500}$ in Gel SAIB (833 mg, 90 w % in EtOH) and PLA (50 mg) were mixed and homogenized by a ball homogenizer (frequency 30 s$^{-1}$, 45 min) to give a clear homogenous solution. PNIPAM coated AuNPs (358 µL, 30 mg Au (84 mg Au/mL by ICP-AES)) were transferred into EtOH by centrifugation (13.400 RPM, 5 min). The supernatant was discarded and replaced three times with EtOH (3×1 mL), the final volume adjusted to 148 µL and added to the SAIB/PLA mixture to give a final nanogel forming matrix composed of SAIB/EtOH/PLA (75:20:5) with 30 mg/mL PNIPAM coated AuNPs.

Figure 15:
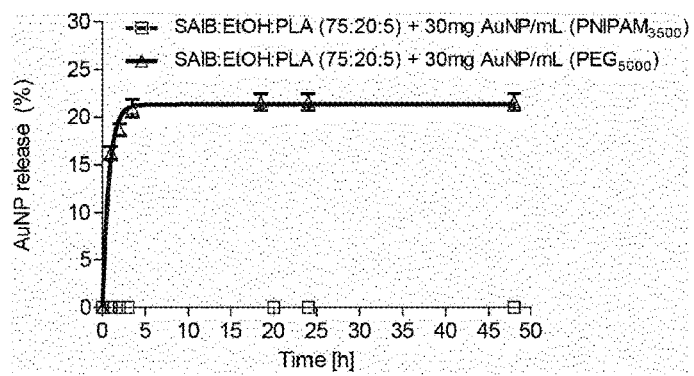
FIG. 15 illustrates the in vitro release profile for SAIB/EtOH/PLA (75:20:5)+30 mg AuNP/mL (PNIPAM coated AuNP) and SAIB/EtOH/PLA (75:20:5)+30 mg AuNP/mL ($PEG_{5000}$ coated AuNP) hydrogels in PBS-buffer/MQ-$H_2O$ at 37° C. Open squares; SAIB/EtOH/PLA (75:20:5)+30 mg AuNP/mL (PNIPAM coated AuNP), open triangles; SAIB/EtOH/PLA (75:20:5)+30 mg AuNP/mL ($PEG_{5000}$ coated AuNP).

SAIB/EtOH/PLA (75:20:5) with 30 mg/mL PNIPAM coated AuNPs (200 µL) were added to a glass vials containing MQ-H$_2$O (10.0 mL, 37° C.) and small aliquots (1.00 mL) were removed as a function of time and replaced with fresh MQ-H$_2$O. The amount of released AuNPs was measured by correlating the UV-vis absorbance at 540 nm with a standard curve based on Au-standards of known concentration. No leakage of PNIPAM coated AuNP was observed within 2 days. Formulations with PEGylated AuNP resulted in approx. 20% leakage within the same time frame (FIG. 15).

Example 6—PEGylated Au Nanoparticles as X-ray Contrast Agent for CT, ConeBeam and ExactTrack Imaging Materials Trisodium citrate dihydrate, was purchased from Sigma-Aldrich (Brøndby, Denmark). MeO-PEG$_{5000}$-SH was purchased from Rapp Polymere GmbH (Tuebingen, Germany) and HAuCl$_4$.3H$_2$O was purchased from Wako Chemicals GmbH (Neuss, Germany).

Au Nanoparticle Formation

PEGylated Au nanoparticles were prepared as described in Example 5.

X-Ray Contrast vs. AuNP Concentration

Figure 16:
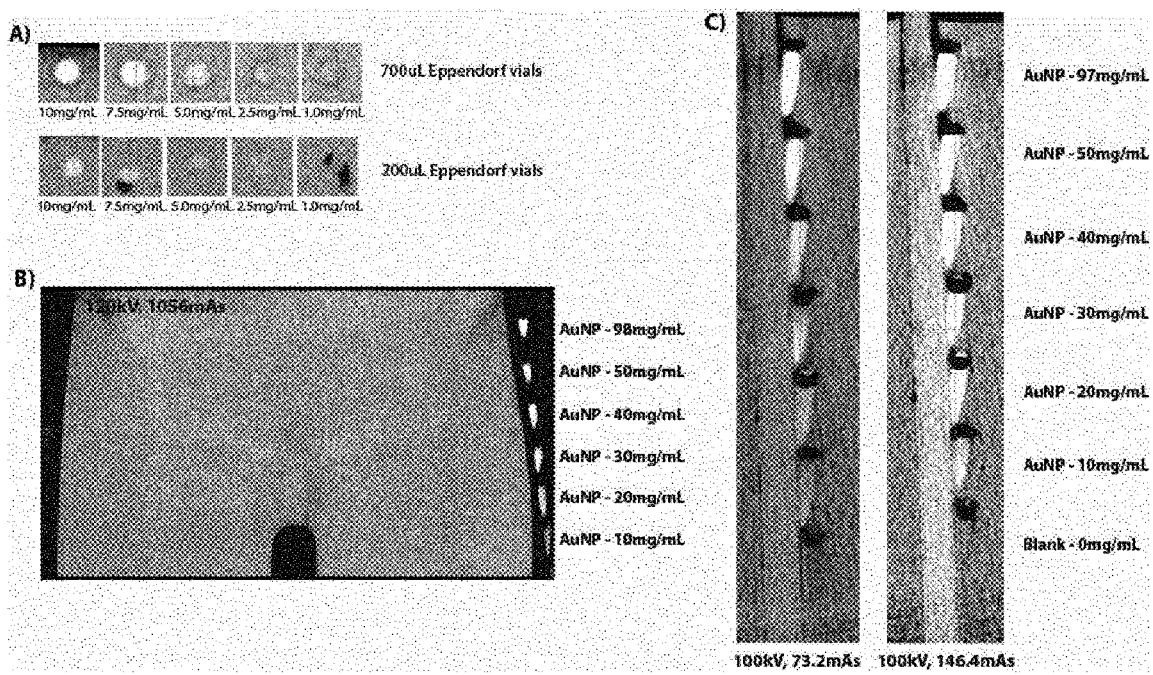
FIG. 16 illustrates the concentration depending X-ray contrast using the ConeBeam imaging modality in either a water- or pelvis phantom. Au nanoparticles; d=40 nm, $PEG_{5000}$. A) X-ray contrast as a function of concentration (1.0, 2.5, 5.0, 7.5 and 10 mg Au/mL) and volume (200 uL vs. 700 uL) in water phantom; B) X-ray contrast as a function of concentration (10, 20, 30, 40, 50 and 98 mg Au/mL (200 uL) in pelvis phantom; C) X-ray contrast as a function of concentration (10, 20, 30, 40, 50 and 97 mg Au/mL (200 uL) in water phantom.
Figure 17:
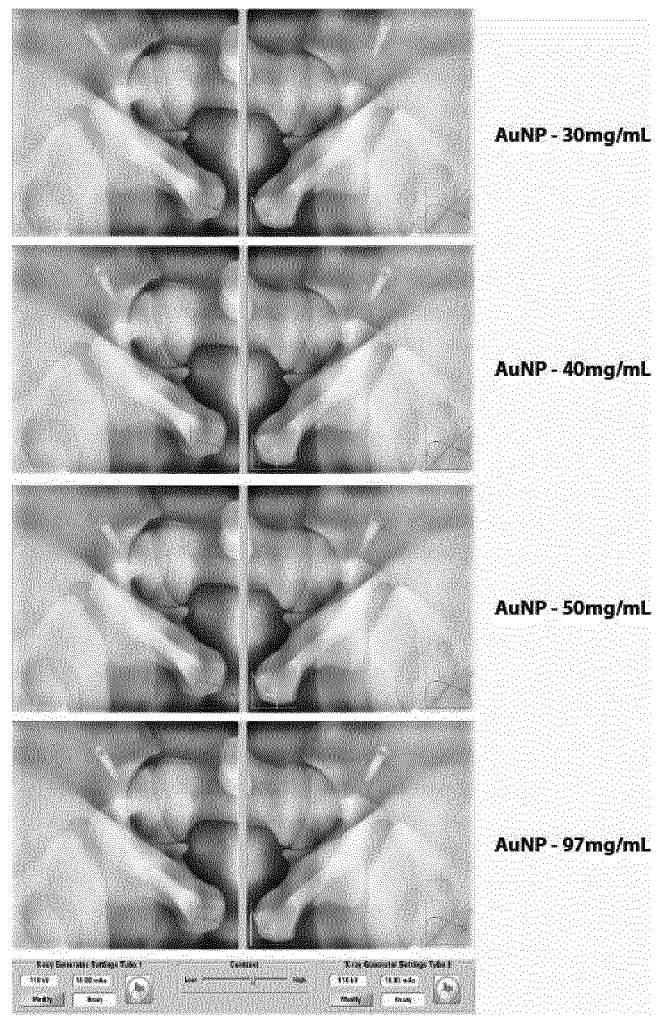
FIG. 17 illustrates the concentration depending X-ray contrast as a function of concentration (30, 40, 50 and 97 mg Au/mL (200 uL) using the ExactTrack imaging modality in a pelvis phantom. Au nanoparticles; d=40 nm, $PEG_{5000}$.
Figure 18:
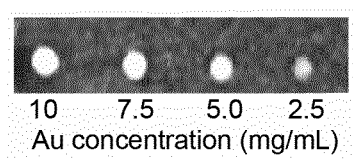
FIG. 18 illustrates the concentration depending X-ray contrast as a function of concentration (2.5, 5.0, 7.5 and 10 mg Au/mL (200 uL) using CT-imaging in a water phantom.

Au nanoparticle stock solution (98 mg Au/mL) was diluted with MQ-H$_2$O to 1.0, 2.5, 5.0, 7.5, 10, 20, 30, 40, and 50 mg Au/mL, respectively, (V=200 uL/700 uL in Eppendorf plastic tubes) and placed in either a water phantom or a pelvis phantom. The concentration depending X-ray contrast was monitored using ConeBeam (FIG. 16), ExactTrack (FIG. 17) and CT-imaging (FIG. 18).

Example 7—Parental Delivery of PEGylated Au Nanoparticles as X-Ray Contrast in Hydrogel Matrixes (Alginate, Pluronics, PCL$_{2700}$-PEG$_{750}$ and SAIB/EtOH/PLA) In Vivo Hydrogel Formulations and Au Nanoparticles Hydrogel matrixes and Au nanoparticles were all prepared as previously described in Example 1-6 above.

Figure 19:
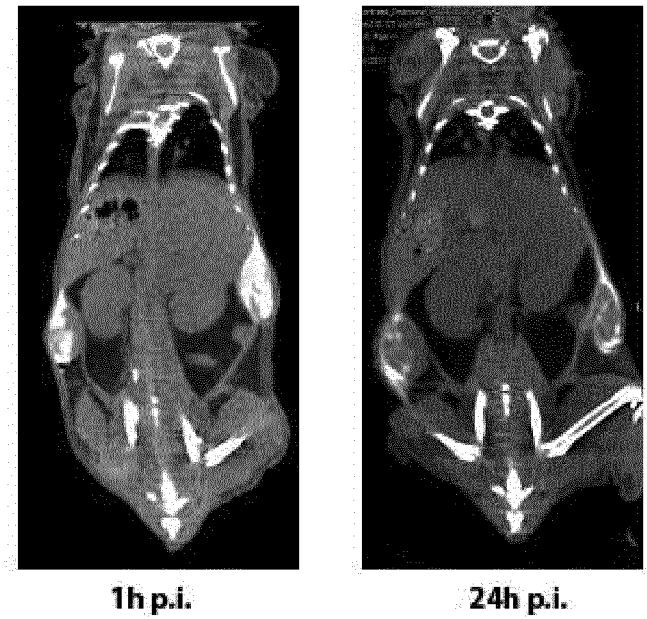
FIG. 19 illustrates Micro-CT scans recorded 1 h and 24 h p.i. of a formulation consisting of 1.7% alginate (w/v) in 10 mM acetate (pH 5.0), 20 mM $Ca^{2+}$, 223.5 mM sucrose and 10 mg Au/mL (d=16 nm, coated with $PEG_{5000}$). Formulation administered by intratumoral injection (injection volume; 2×150 μL) to H-727 xenografts tumour bearing mice with tumours in each flank

A) A formulation consisting of 1.7% alginate (w/v) in 10 mM acetate (pH 5.0), 20 mM Ca$^{2+}$, 223.5 mM sucrose and 10 mg Au/mL (d=16 nm, coated with PEG$_{5000}$) was administered by intratumoral injection (injection volume; 2×150 µL) to H-727 xenografts tumour bearing mice with tumours in each flank. Micro-CT scans were recorded 1- and 24 h p.i. (FIG. 19).

Figure 20:
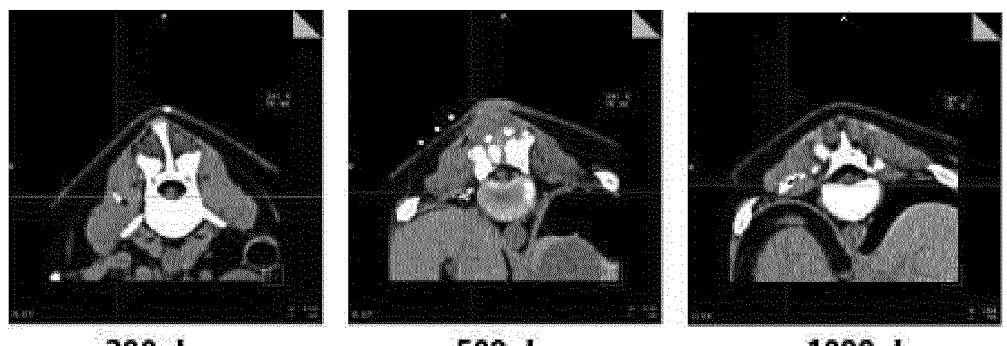
FIG. 20 illustrates CT-scans recorded 1 h p.i of a formulation consisting of Pluronics F-127 (18.85% w/w) and 10 mg Au/mL (d=16 nm, coated with $PEG_{5000}$) in sterile MQ-$H_2O$. Formulation administered by intramuscular injection (injection volume; 200 μL, 500 μL or 1000 μL) in canine.

B) A formulation consisting of Pluronics F-127 (18.85 w %) and 10 mg Au/mL (d=16 nm, coated with $PEG_{5000}$) in sterile $MQ-H_2O$ was prepared as previously described and administered by intramuscular injection (injection volume; 200 μL, 500 μL or 1000 μL) in canine. CT-scans were recorded 1 h p.i. (FIG. 20).

Figure 21:
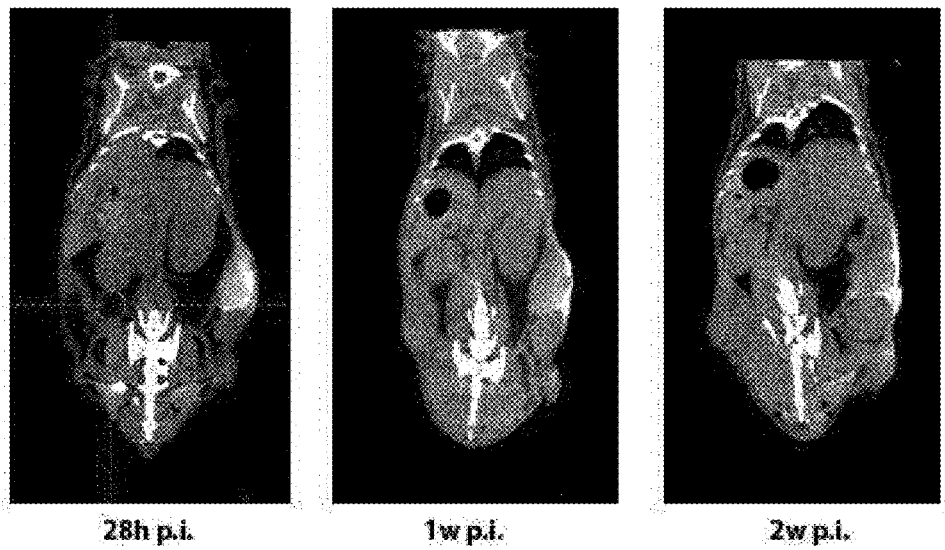
FIG. 21 illustrates Micro-CT scans recorded 28 h, 1 weeks and 2 weeks p.i. of a formulation consisting of $PCL_{2700}$-$PEG_{750}$ (25 w %) and 10 mg Au/mL (d=20 nm, coated with $PEG_{5000}$) in sterile PBS-buffer. Formulation administered by subcutaneous injection (injection volume; 200 μL) to H-727 xenografts tumour bearing mice with tumours in each flank.

C) A formulation consisting of $PCL_{2700}$-$PEG_{750}$ (25 w %) and 10 mg Au/mL (d=20 nm, coated with $PEG_{5000}$) in sterile PBS-buffer was prepared as previously described and administered by subcutaneous injection (injection volume; 200 μL) to H-727 xenografts tumour bearing mice with tumours in each flank using a 26 G needle. Micro-CT scans were recorded 28 h, 1- and 2 weeks p.i. (FIG. 21).

Figure 22:
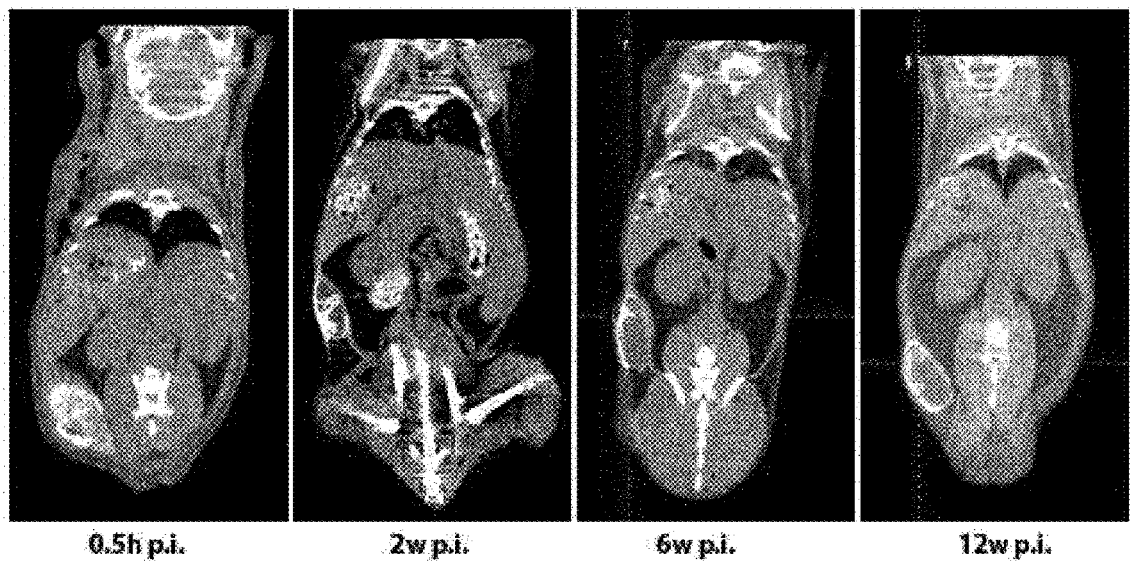
FIG. 22 illustrates Micro-CT scans recorded 0.5 h, 2, 6 and 12 weeks p.i of a formulation consisting of SAIB/EtOH/PLA (12 kDa) (75:20:5) and 10 mg Au/mL (d=40 nm, coated with $PEG_{5000}$). Formulation administered by subcutaneous injection (injection volume; 200 μL) to healthy NMRI-mice.

D) A formulation consisting of SAIB/EtOH/PLA (12 kDa) (75:20:5) and 10 mg Au/mL (d=40 nm, coated with $PEG_{5000}$) was prepared as previously described and administered by subcutaneous injection (injection volume; 200 μL) to healthy NMRI-mice. Micro-CT scans were recorded over a period of 12 weeks p.i. (FIG. 22).

The formulations of Examples 1 to 6 were all free-flowing liquids that can be injected through 25 G hypodermic needles with none or very low back pressure.

The invention claimed is:

1. A method of recording an X-ray image of the body of a mammal, comprising the steps of:
   a. providing a formulation comprising a plurality of solid in-organic particles and an organic gel-forming system, wherein the solid in-organic particles have a (number) average diameter of 1-500 nm and comprise or consist of a compound detectable by X-ray imaging, and the organic gel-forming system undergoes gel-formation when injected into a body of a mammal, the formulation is imagable, the plurality of solid in-organic particles comprise one or more selected from the group consisting of X-ray contrast agents, radioactive compounds, paramagnetic compounds, fluorescent compounds, ferromagnetic compounds and mixtures thereof, and the formulation has a viscosity less than 10,000 centipoise (cP) at 20° C.;
   b. administering the formulation to a predetermined location of the mammal; and
   c. recording X-ray-based images of at least a part of the body which comprises the predetermined location.

2. The method of recording an X-ray image of the body of a mammal according to claim 1, wherein the X-ray-based images are Computed Tomography (CT)-images.

3. A method of joint radiotherapy and X-ray imaging of a target tissue in a mammal, comprising the steps of:
   a, providing a formulation comprising a plurality of solid in-organic particles and an organic gel-forming system, wherein the solid in-organic particles have a (number) average diameter of 1-500 nm and comprise or consist of a compound detectable by X-ray imaging, the organic gel-forming system undergoes gel-formation when injected into a body of a mammal, the formulation is imagable, the plurality of solid in-organic particles comprise one or more selected from the group consisting of X-ray contrast agents, radioactive compounds, paramagnetic compounds, fluorescent compounds, ferromagnetic compounds and mixtures thereof, and the formulation has a viscosity less than 10,000 centipoise (cP) at 20° C.;
   b. administering the formulation to a predetermined target tissue of the mammal;
   c. recording X-ray-based images of at least a part of the body which comprises the target tissue, thereby providing a definition of the target tissue; and
   d. using the definition of the target tissue obtained in c. to direct external beam radiotherapy to the target tissue.

4. The method according to claim 3, wherein the target tissue comprises undesirably growing cells.

5. The method according to claim 3, wherein the target tissue comprises tumor cells.

6. The method according to claim 3, wherein steps c. and d. are performed simultaneously.

7. The method of joint radiotherapy and X-ray imaging of a target tissue in a mammal according to claim 3, wherein the X-ray-based images are Computed Tomography (CT)-images.

8. A method for directing local administration of a pharmaceutically active agent to a target tissue in a mammal, comprising the steps of:
   a. providing a formulation comprising a plurality of solid in-organic particles and an organic gel-forming system, wherein the solid in-organic particles have a (number) average diameter of 1-500 nm and comprise or consist of a detectable compound; optionally detectable by X-ray imaging, the organic gel-forming system undergoes gel-formation when injected into the body of a mammal, the formulation is imagable; the plurality of solid in-organic particles comprise one or more selected from the group consisting of X-ray contrast agents, radioactive compounds, paramagnetic compounds, fluorescent compounds, ferromagnetic compounds, and mixtures thereof, and the formulation has a viscosity less than 10,000 centipoise (cP) at 20° C.;
   b. administering the formulation to a predetermined target tissue of the mammal;
   c. recording images of at least a part of the body which comprises the target tissue, thereby providing a definition of the target tissue; and
   d. using the definition of the target tissue obtained in step c. to direct local administration of a pharmaceutically active agent to the target tissue.

9. The method for directing local administration of a pharmaceutically active agent to a target issue in a mammal according to claim 8, wherein the X-ray-based images are Computed Tomography (CT)-images.

* * * * *

UNITED STATES PATENT AND TRADEMARK OFFICE
CERTIFICATE OF CORRECTION

PATENT NO. : 10,434,192 B2
APPLICATION NO. : 16/050318
DATED : October 8, 2019
INVENTOR(S) : Rasmus Irving Jolck et al.

It is certified that error appears in the above-identified patent and that said Letters Patent is hereby corrected as shown below:

Claim 1, Column 35, Line 33, please delete the word "imagable" and replace with "imageable".
Claim 3, Column 36, Line 1, please delete the word "imagable" and replace with "imageable".
Claim 8, Column 36, Line 35, please delete the word "imagable" and replace with "imageable".

Signed and Sealed this
Nineteenth Day of November, 2019

Andrei Iancu
*Director of the United States Patent and Trademark Office*